US009217014B2

(12) United States Patent
James, Jr. et al.

(10) Patent No.: US 9,217,014 B2
(45) Date of Patent: Dec. 22, 2015

(54) ANTIFUNGAL AGENTS AND USES THEREOF

(71) Applicant: Cidara Therapeutics, Inc., San Diego, CA (US)

(72) Inventors: Kenneth Duke James, Jr., Mebane, NC (US); Christopher Patrick Laudeman, Durham, NC (US); Navdeep Balkrishna Malkar, Cary, NC (US); Balasingam Radhakrishnan, Chapel Hill, NC (US)

(73) Assignee: Cidara Therapeutics, Inc., San Diego, CA (US)

( * ) Notice: Subject to any disclaimer, the term of this patent is extended or adjusted under 35 U.S.C. 154(b) by 0 days.

(21) Appl. No.: 14/242,192

(22) Filed: Apr. 1, 2014

(65) Prior Publication Data

US 2015/0024997 A1    Jan. 22, 2015

Related U.S. Application Data

(63) Continuation of application No. 13/886,972, filed on May 3, 2013, now Pat. No. 8,722,619, which is a continuation of application No. PCT/US2012/027451, filed on Mar. 2, 2012.

(60) Provisional application No. 61/448,807, filed on Mar. 3, 2011.

(51) Int. Cl.
| | | |
|---|---|---|
| *A61K 38/00* | (2006.01) | |
| *A61K 38/08* | (2006.01) | |
| *C07K 7/00* | (2006.01) | |
| *C07K 7/50* | (2006.01) | |
| *C07K 7/06* | (2006.01) | |
| *C07K 7/54* | (2006.01) | |
| *C07K 7/56* | (2006.01) | |
| *C07K 7/60* | (2006.01) | |
| *C07K 7/64* | (2006.01) | |
| *A61K 38/04* | (2006.01) | |

(52) U.S. Cl.
CPC ... *C07K 7/60* (2013.01); *C07K 7/56* (2013.01); *C07K 7/64* (2013.01); *A61K 38/00* (2013.01); *A61K 38/04* (2013.01); *A61K 38/08* (2013.01); *C07K 7/00* (2013.01); *C07K 7/50* (2013.01); *C07K 7/54* (2013.01)

(58) Field of Classification Search
None
See application file for complete search history.

(56) References Cited

U.S. PATENT DOCUMENTS

| | | | |
|---|---|---|---|
| 5,378,804 A | 1/1995 | Balkovec et al. | |
| 5,399,552 A | 3/1995 | Bouffard | |
| 5,514,651 A | 5/1996 | Balkovec et al. | |
| 5,516,756 A | 5/1996 | Balkovec et al. | |
| 5,541,160 A * | 7/1996 | Balkovec et al. | 514/3.3 |
| 5,652,213 A | 7/1997 | Jamison et al. | |
| 5,741,775 A | 4/1998 | Balkovec et al. | |
| 5,854,213 A | 12/1998 | Bouffard | |
| 5,948,753 A | 9/1999 | Balkovec et al. | |
| 6,030,944 A | 2/2000 | Bouffard et al. | |
| 6,268,338 B1 | 7/2001 | Balkovec et al. | |
| 6,506,726 B1 | 1/2003 | Dobbins et al. | |
| 6,821,951 B2 | 11/2004 | Schwier et al. | |
| 8,722,619 B2 | 5/2014 | James, Jr. et al. | |
| 2005/0026819 A1 | 2/2005 | Kaniga | |
| 2007/0231258 A1 | 10/2007 | Perakyla et al. | |

FOREIGN PATENT DOCUMENTS

| | | | |
|---|---|---|---|
| WO | WO-96/08507 A1 | 3/1996 | |
| WO | WO-2010/032011 A2 | 3/2010 | |
| WO | WO-2010/128096 A1 | 11/2010 | |

OTHER PUBLICATIONS

Fujie et al., Bioorganic & Medicinal Chemistry Letters (2001) 11, 399-402.*
Denning, "Echinocandin antifungal drugs," Lancet. 362(9390):1142-51 (2003).
English translation of Search Report for Chinese Application No. 201280021321.9, dated Jan. 6, 2015 (7 pages).
Bouffard et al., "Synthesis and antifungal activity of novel cationic pneumocandin Bo derivatives," J Med Chem. 37(2): 222-5 (1994).
Cuenca-Estrella et al., "Susceptibility of fluconazole-resistant clinical isolates of *Candida* spp. to echinocandin LY303366, itraconazole and amphotericin B," J Antimicrob Chemother. 46(3): 475-7 (2000).
Espinel-Ingroff, "Comparison of In vitro activities of the new triazole SCH56592 and the echinocandins MK-0991 (L-743,872) and LY303366 against opportunistic filamentous and dimorphic fungi and yeasts," J Clin Microbiol. 36(10): 2950-6 (1998).
International Search Report and Written Opinion for International Application No. PCT/US12/27451, mailed Jun. 20, 2012 (16 pages).
Jamison et al., "The synthesis and antifungal activity of nitrogen containing hemiaminal ethers of LY303366," J Antibiot (Tokyo). 51(2): 239-42 (1998).
Verweij et al., "Efficacy of LY303366 against amphotericin B-susceptible and -resistant *Aspergillus fumigatus* in a murine model of invasive aspergillosis," Antimicrob Agents Chemother. 42(4): 873-78 (1998).
Uzun et al., "In vitro activity of a new echinocandin, LY303366, compared with those of amphotericin B and fluconazole against clinical yeast isolates," Antimicrob Agents Chemother. 41(5): 1156-7 (1997).
Partial supplementary European Search Report for European Patent Application No. 12751994.0, issued Mar. 10, 2015 (5 pages).
English translation of Office Action for Japanese Patent Application No. 2013-556894, mailed Apr. 21, 2015 (2 pages).
Extended European Search Report for International Patent Application No. 12751994.0, dated Jul. 27, 2015 (8 pages).

\* cited by examiner

*Primary Examiner* — Marcela M Cordero Garcia
*Assistant Examiner* — Catherine Mader
(74) *Attorney, Agent, or Firm* — Clark & Elbing LLP

(57) ABSTRACT

The invention features echinocandin class compounds. The compounds can be useful for the treatment of fungal infections.

34 Claims, 3 Drawing Sheets

Figure 1

| Organism | | Anidulafungin | | Caspofungin | | Compound 1 | | Compound 16 | | Amphotericin B | |
|---|---|---|---|---|---|---|---|---|---|---|---|
| Human Serum % present | | 0 | 50 | 0 | 50 | 0 | 50 | 0 | 50 | 0 | 50 |
| *Aspergillus candidus* 450 ATCC[2] 13686 | MEC[3] | ≤0.015 | NG | ≤0.015 | NG | ≤0.015 | NG | ≤0.015 | NG | ≤0.06 | NG |
| | MIC[4] | ≤0.015 | | ≤0.015 | | ≤0.015 | | ≤0.015 | | ≤0.06 | |
| *Aspergillus clavatus* 638 ATCC 10058[5] | MEC | ≤0.015 | 0.125 | 0.125 | 0.06 | 0.03 | 0.125 | 0.03 | 0.125 | ≤0.06 | ≤0.06 |
| | MIC | 4 | >16 | 2 | >16 | 4 | >16 | 4 | >16 | | |
| *Aspergillus flavus* 122 ATCC 22546 | MEC | ≤0.015 | 0.125 | 0.06 | 0.25 | ≤0.015 | 0.125 | ≤0.015 | 0.06 | 1 | 0.5 |
| | MIC | >16 | >16 | >16 | >16 | >16 | >16 | >16 | >16 | | |
| *Aspergillus fumigatus* 891 ATCC 204305 | MEC | ≤0.015 | 0.125 | 0.125 | 0.125 | ≤0.015 | 0.06 | ≤0.015 | 0.06 | 1 | 1 |
| | MIC | >16 | >16 | >16 | >16 | >16 | >16 | >16 | >16 | | |
| *Aspergillus niger* 624 ATCC 16888 | MEC | ≤0.015 | 0.06 | 0.06 | 0.06 | ≤0.015 | 0.03 | ≤0.015 | 0.015 | 0.125 | 0.25 |
| | MIC | ≤0.015 | 0.125 | 0.25 | 0.125 | ≤0.015 | 0.06 | ≤0.015 | 0.03 | | |
| *Aspergillus ochraceus* 625 ATCC 96919 | MEC | 0.03 | 0.125 | 0.06 | 0.06 | 0.03 | 0.06 | 0.03 | 0.03 | 2 | 2 |
| | MIC | 0.06 | >16 | 0.125 | >16 | 0.125 | >16 | 0.125 | >16 | | |
| *Aspergillus fumigatus* 5280 ATCC MYA-3626 | MEC | ≤0.015 | 0.125 | 0.125 | 0.25 | ≤0.015 | 0.125 | ≤0.015 | 0.06 | 1 | 1 |
| | MIC | >16 (≤0.015)[1] | >16 | >16 | >16 | >16 | >16 | >16 | >16 | (0.5-4)[6] | |

1. Clinical and Laboratory Standards Institute Minimal Effective Concentration (MEC) quality control range.
2. American Type Culture Collection.
3. Minimal Effective Concentration.
4. Minimal Inhibitory Concentration.
5. Plate not readable at 48 hours, but could read results after 68 hours of incubation.
6. Clinical and Laboratory Standards Institute Minimal Inhibitory Concentration (MIC) quality control range.

Figure 2

| Organism | | Anidulafungin | | Caspofungin | | Compound 1 | | Compound 16 | | Amphotericin B | |
|---|---|---|---|---|---|---|---|---|---|---|---|
| Human Serum % present | | 0 | 50 | 0 | 50 | 0 | 50 | 0 | 50 | 0 | 50 |
| Candida albicans 104 ATCC[3] 90028 | 24 hr | ≤0.015 | NG | 0.06 | NG | 0.03 | NG | 0.03 | NG | ≤0.06 | 50 |
| | 48 hr | ≤0.015 | | 0.06 | | 0.03 | | 0.03 | | 0.125 | NG |
| Candida glabrata 635 ATCC 90030 | 24 hr | 0.03 | 0.5 | 0.125 | 0.25 | 0.03 | 0.125 | 0.03 | 0.06 | 0.06 | 0.125 |
| | 48 hr | 0.03 | 0.5 | 0.125 | 0.25 | 0.03 | 0.125 | 0.03 | 0.06 | 0.25 | 0.25 |
| Candida guilliermondii 6282 ATCC 34134 | 24 hr | 1 | NG | 0.25 | NG | 0.5 | NG | 0.5 | NG | ≤0.06 | NG |
| | 48 hr | 2 | | >16[4] | | 2 | | 1 | | ≤0.06 | |
| Candida krusei 629 ATCC 14243 | 24 hr | 0.03 | NG | 0.25 | NG | 0.03 | NG | 0.03 | NG | 0.25 | NG |
| | 48 hr | 0.06 | | 0.5 | | 0.03 | | 0.03 | | 0.5 | |
| Candida Lusitaniae 631 ATCC 34134 | 24 hr | 0.125 | NG | 0.25 | NG | 0.25 | NG | 0.25 | NG | ≤0.06 | NG |
| | 48 hr | 0.125 | | 0.25 | | 0.25 | | 0.25 | | ≤0.06 | |
| Candida parapsilosis 2323 ATCC 22019 | 24 hr | 0.5 | NG | 0.25 | NG | 0.25 | NG | 0.25 | NG | 0.25 | NG |
| | 48 hr | 0.5 (0.25-2)[1] (0.5-2)[2] | | 0.5 (0.25-1)[1] (0.5-4)[2] | | 0.5 | | 0.5 | | 0.5 (0.25-2)[1] (0.5-4)[2] | |
| Candida tropicalis 4783 ATCC 90874 | 24 hr | ≤0.015 | NG | 0.06 | NG | ≤0.015 | NG | ≤0.015 | NG | 0.25 | NG |
| | 48 hr | ≤0.015 | | 0.06 | | ≤0.015 | | ≤0.015 | | 0.25 | |

1. Clinical and Laboratory Standards Institute Minimal Inhibitory Concentration (MIC) quality control range for 24 hr reading.
2. Clinical and Laboratory Standards Institute Minimal Inhibitory Concentration (MIC) quality control range for 48 hr reading.
3. American Type Culture Collection.
4. Reduced growth from 0.5-16 μg/mL, but did not achieve the CLSI-described endpoint.

ANTIFUNGAL AGENTS AND USES THEREOF

CROSS REFERENCE TO RELATED APPLICATIONS

This application is a continuation of U.S. patent application Ser. No. 13/886,972, filed May 3, 2013, which is a continuation of International Patent Application No. PCT/US2012/027451, filed Mar. 2, 2012, which claims the benefit of U.S. Provisional Application No. 61/448,807, filed Mar. 3, 2011, each of which is incorporated herein by reference.

BACKGROUND OF THE INVENTION

This invention relates to the field of treatment of fungal infections.

The need for novel antifungal treatments is significant, and is especially critical in the medical field. Immunocompromised patients provide perhaps the greatest challenge to modern health care delivery. During the last three decades there has been a dramatic increase in the frequency of fungal infections in these patients (Herbrecht, Eur. J. Haematol., 56:12, 1996; Cox et al., Curr. Opin. Infect. Dis., 6:422, 1993; Fox, ASM News, 59:515, 1993). Deep-seated mycoses are increasingly observed in patients undergoing organ transplants and in patients receiving aggressive cancer chemotherapy (Alexander et al., Drugs, 54:657, 1997). The most common pathogens associated with invasive fungal infections are the opportunistic yeast, *Candida albicans*, and the filamentous fungus, *Aspergillus fumigatus* (Bow, Br. J. Haematol., 101:1, 1998; Warnock, J. Antimicrob. Chemother., 41:95, 1998). There are an estimated 200,000 patients per year who acquire nosocomial fungal infections (Beck-Sague et al., J. Infect. Dis., 167:1247, 1993). Also adding to the increase in the numbers of fungal infections is the emergence of Acquired Immunodeficiency Syndrome (AIDS) where virtually all patients become affected with some form of mycoses during the course of the disease (Alexander et al., Drugs, 54:657, 1997; Hood et al., J. Antimicrob. Chemother., 37:71, 1996). The most common organisms encountered in these patients are *Cryptococcus neoformans, Pneumocystis carinii*, and *C. albicans* (HIV/AIDS Surveillance Report, 1996, 7(2), Year-End Edition; Polis, M. A. et al., AIDS: Biology, Diagnosis, Treatment and Prevention, fourth edition, 1997). New opportunistic fungal pathogens such as *Penicillium marneffei, C. krusei, C. glabrata, Histoplasma capsulatum*, and *Coccidioides immitis* are being reported with regularity in immunocompromised patients throughout the world.

The development of antifungal treatment regimens has been a continuing challenge. Currently available drugs for the treatment of fungal infections include amphotericin B, a macrolide polyene that interacts with fungal membrane sterols, flucytosine, a fluoropyrimidine that interferes with fungal protein and DNA biosynthesis, and a variety of azoles (e.g., ketoconazole, itraconazole, and fluconazole) that inhibit fungal membrane-sterol biosynthesis (Alexander et al., Drugs, 54:657, 1997). Even though amphotericin B has a broad range of activity and is viewed as the "gold standard" of antifungal therapy, its use is limited due to infusion-related reactions and nephrotoxicity (Warnock, J. Antimicrob. Chemother., 41:95, 1998). Flucytosine usage is also limited due to the development of resistant microbes and its narrow spectrum of activity. The widespread use of azoles is causing the emergence of clinically-resistant strains of *Candida* spp. Due to the problems associated with the current treatments, there is an ongoing search for new treatments.

When the echinocandin caspofungin was approved for sale in 2001, it represented the first new class of antifungal agents to be approved in over a decade. Since that time, two other echinocandin antifungals, anidulafungin and micafungin, have been approved in various markets. Each agent in this class of compound acts by inhibition of $\beta$-1,3-glucan synthase, which is a key enzyme in the synthesis of glucan in the cell wall of many fungi. All three of these drugs are made semisynthetically, starting with natural products obtained through fermentation.

The echinocandins are a broad group of antifungal agents that typically are comprised of a cyclic hexapeptide and lipophilic tail, the latter of which is attached to the hexapeptide core through an amide linkage. Although many echinocandins are natural products, the clinically relevant members of this class have all been semisynthetic derivatives. Although the naturally occurring echinocandins possess some degree of anti-fungal activity, they have not been suitable as therapeutics, primarily because of poor aqueous solubility, insufficient potency, and/or hemolytic action. The approved echinocandins are the products of intense efforts to generate derivatives that maintain or improve upon the glucan synthase inhibition, but do not cause the hemolytic effects. As therapeutic agents, they are attractive compounds in terms of their systemic half-lives, large therapeutic windows, safety profiles, and relative lack of interactions with other drugs. Unfortunately, the poor aqueous solubility and poor intestinal absorption of these compounds have relegated them to delivery by intravenous infusion. Although patients receiving these drugs are often hospitalized with serious infections, the ability to transition patients from intravenous delivery in a hospital setting to oral delivery in a home setting would be very desirable, especially considering the course of the regimen commonly exceeds 14 days. In addition, an oral echinocandin may expand the use of this drug class to include patients that present with mild fungal infections.

SUMMARY OF THE INVENTION

The present invention features derivatives of echinocandin antifungals that can have increased aqueous solubility. More specifically, the invention features echinocandin class compounds that have been modified such that they can exhibit (i) activity against one or more fungal species or genera; (ii) increased aqueous solubility and/or amphiphilicity; (iii) have an increased therapeutic index; (iv) suitability for topical administration; (v) suitability for intravenous administration; (vi) have an increased volume of distribution; and/or (vii) have an increased elimination half-life.

The invention features compounds of formula (I):

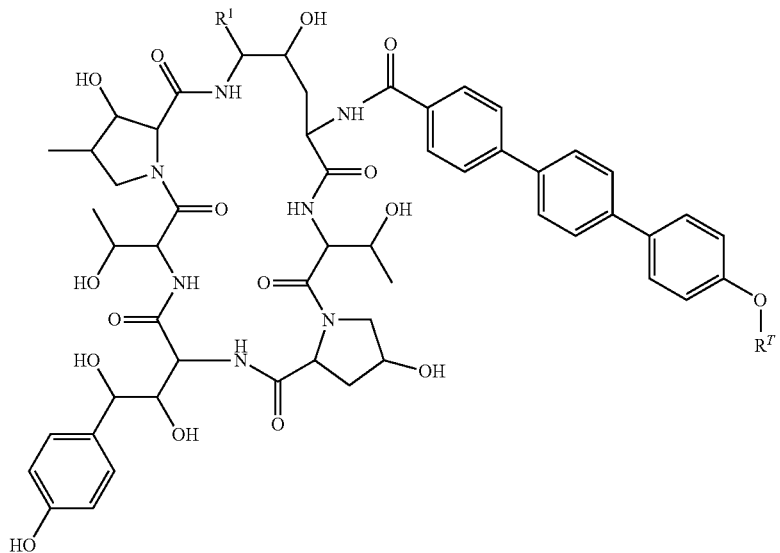

In formula (I), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aO]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NH_2$, $NHR^{A1}$, $NR^{A1}R^{A2}$, $NR^{A1}R^{A2}R^{A3}$, or $NHCH_2(CH_2)_vZ_1$; $X_2$ is OH, $OR^{B1}$, or $OCH_2(CH_2)_vZ_1$; $X_3$ is $NH_2$, $NHR^{C1}$, $NR^{C1}R^{C2}$, or $NR^{C1}R^{C2}R^{C3}$, or $NHCH_2(CH_2)_vZ_1$; $X_4$ is $NR^{D1}R^{D2}R^{D3}$ or $NHCH_2(CH_2)_vZ_1$; each $X_5$ is, independently, selected from OH, $OR^{E1}$, $NH_2$, $NHR^{E1}$, $NR^{E1}R^{E2}$, $NR^{E1}R^{E2}R^{E3}$, $OCH_2(CH_2)_vZ_1$, and $NHCH_2(CH_2)_vZ_1$; $X_6$ is selected from $NR^{F1}R^{F2}R^{F3}$ or $Z_1$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); v is an integer from 1 to 3 (e.g., 1, 2, or 3); each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$; $Z_1$ is selected from:

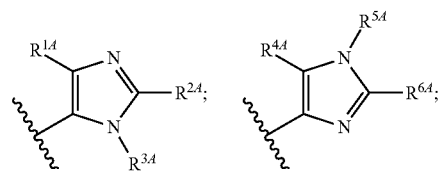

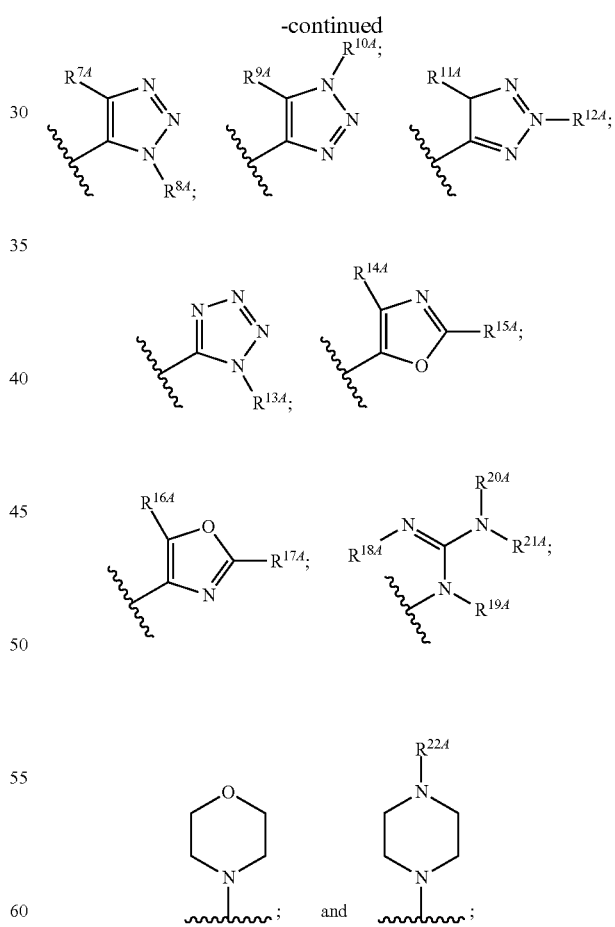

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In certain embodiments, the compound of formula (I) is further described by formula (Ia):

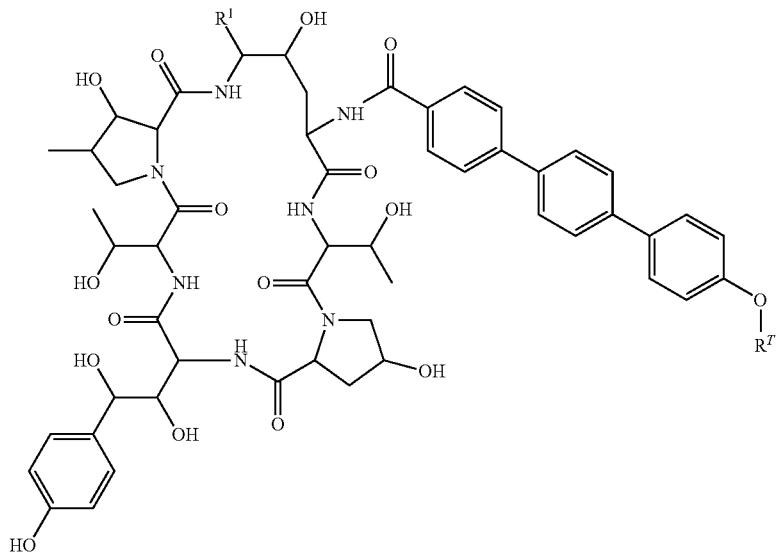

In formula (Ia), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aO]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NH_2$, $NHR^{A1}$, $NR^{A1}R^{A2}$, or $NR^{A1}R^{A2}R^{A3}$; $X_2$ is OH or $OR^{B1}$; $X_3$ is $NH_2$, $NHR^{C1}$, $NR^{C1}R^{C2}$, or $NR^{D1}R^{D2}R^{D3}$; $X_4$ is $NR^{D1}R^{D2}R^{D3}$; each $X_5$ is, independently, selected from OH, $OR^{E1}$, $NH_2$, $NHR^{E1}$, $NR^{E1}R^{E2}$, and $NR^{E1}R^{E2}R^{E3}$; $X_6$ is selected from $NR^{F1}R^{F2}R^{F3}$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); and each of $R^{A1}$, $R^{A2}$, $R^{A3}$, $R^{B1}$, $R^{C1}$, $R^{C2}$, $R^{C3}$, $R^{C1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$, or a pharmaceutically acceptable salt thereof. In particular embodiments of the compounds of formula (I) and (Ia), one of $X_1$, $X_3$, $X_4$, and $X_5$ is selected from $N(CH_3)_3^+$ and $N(CH_2CH_3)_3^+$. In certain embodiments of the compounds of formula (I) and (Ia), $R^1$ is $NHCH[CH_2CH_2N(CH_3)_3^+]_2$, $NHCH_2CH_2OCH[CH_2CH_2N(CH_3)_3^+]_2$, or $NHCH_2CH_2OCH[CH_2CH_2N(CH_3)_3^+][CH_2CH_2OCH_2CH_2OH]$.

In still other embodiments, the compound of formula (I) is further described by formula (Ib):

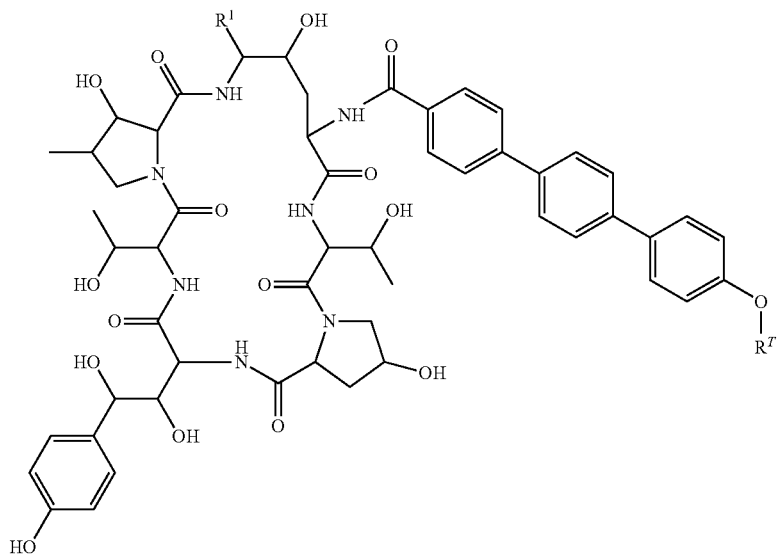

In formula (Ib), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aO]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^T$ is n-pentyl, sec-pentyl, or iso-pentyl; $X_1$ is $NHCH_2(CH_2)_vZ_1$; $X_2$ is $OCH_2(CH_2)_vZ_1$, $X_3$ is $NHCH_2(CH_2)_vZ_1$, $X_4$ is $NHCH_2(CH_2)_vZ_1$; each $X_5$ is, independently, selected from $OCH_2(CH_2)_vZ_1$ and $NHCH_2(CH_2)_vZ_1$; $X_6$ is $Z_1$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); v is an integer from 1 to 3 (e.g., 1, 2, or 3); $Z_1$ is selected from:

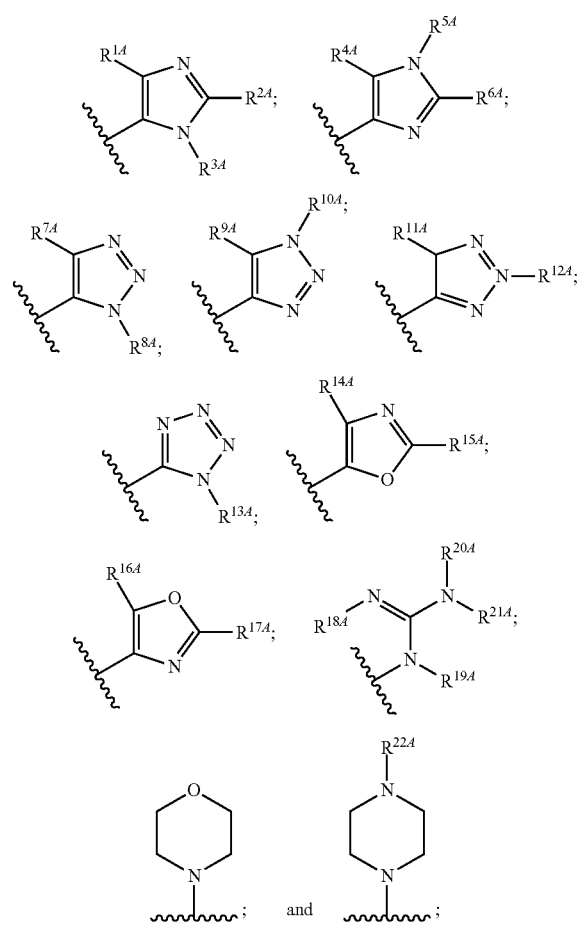

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In one particular embodiment of the compounds of formula (I), (Ia), and (Ib), the compound is further described by one of the formulas:

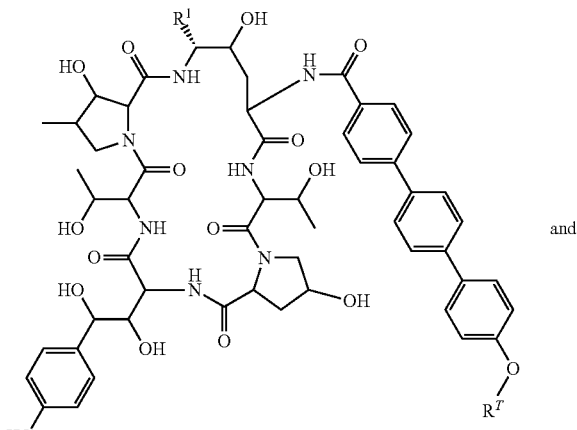

and

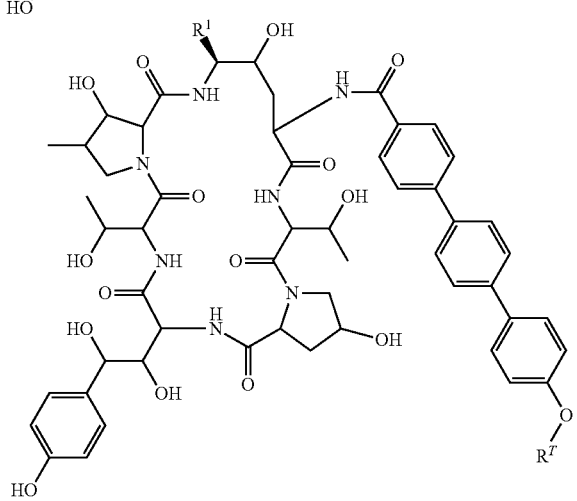

wherein $R^1$ and $R^T$ are as described above.

The invention further features compounds of formula (II):

(II)

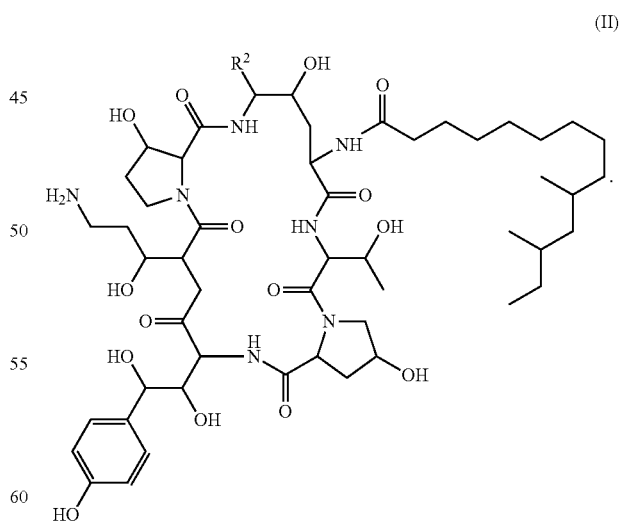

In formula (II), $R^2$ is $NH(CH_2CH_2O)_sCH_2CH_2X_8$, $NH(CH_2CH_2CH_2O)_sCH_2CH_2X_8$, $NH(CH_2CH_2NH)_tCH_2CH_2X_9$, $NH[CH_2(CH_2)_aO]_bCH\{CH_2[OCH_2(CH_2)_c]_dX_9\}_2$, $O[CH_2(CH_2)_aO]_bCH\{CH_2[OCH_2(CH_2)_c]_dX_9\}_2$, $NHCH_2(CH_2)_uX_{10}$, or $OCH_2(CH_2)_uX_{10}$; $X_8$ is OH, $OR^{G1}$, $NH_2$, $NHR^{G1}$, $NR^{G1}R^{G2}$, $NR^{G1}R^{G2}R^{G3}$, $OCH_2(CH_2)_wZ_2$, or $NHCH_2(CH_2)_uX_{10}$; $X_8$ is OH, independently, selected from OH, $OR^{H1}$, $NHR^{H1}$, $NR^{H1}R^{H2}$, $NR^{H1}R^{H2}R^{H3}$, $OCH_2(CH_2)_wZ_2$, and $NHCH_2(CH_2)_uZ_2$; $X_{10}$ is selected from $NR^{J1}R^{J2}R^{J3}$ or $Z_2$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); s is an integer from 1 to 5 (e.g., 1, 2, 3, 4, or 5); t is an integer from 1 to 5 (e.g., 1, 2, 3, 4, or 5); u is an integer from 1 to 3 (e.g., 1, 2, or 3); each of $R^{G1}$, $R^{G2}$, $R^{G3}$, $R^{H1}$, $R^{H2}$, $R^{H3}$, $R^{J1}$, $R^{J2}$, and $R^{J3}$ is, independently, selected from $CH_3$, $CH_2CH_3$, $CH_2CH_2CH_3$, and $CH(CH_3)_2$; w is an integer from 1 to 3 (e.g., 1, 2, or 3); $Z_2$ is selected from

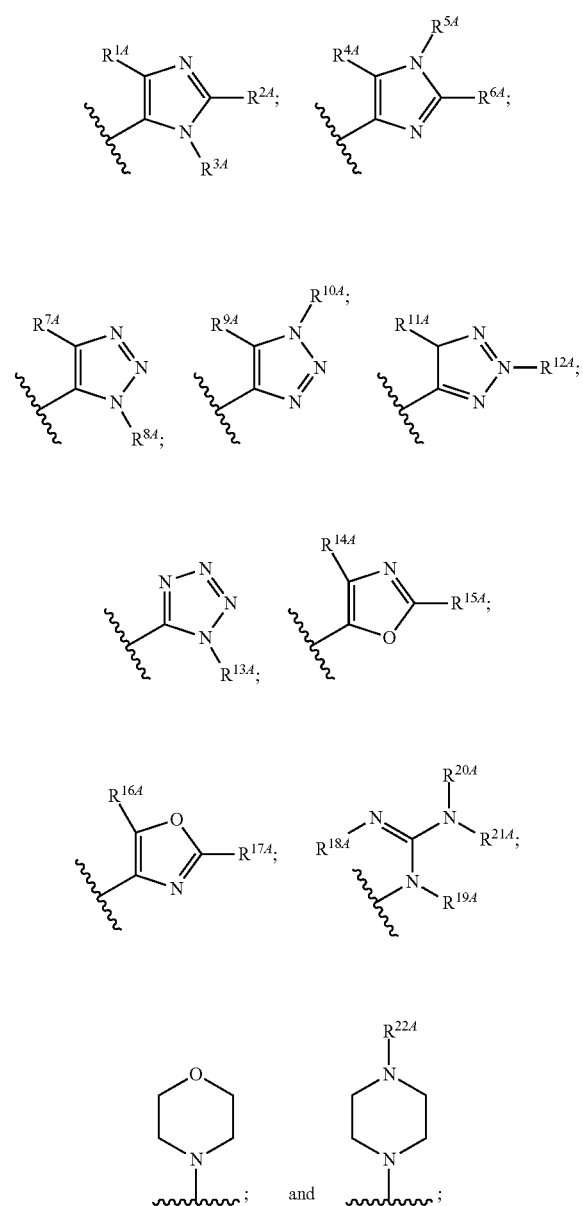

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In certain embodiments, the compound of formula (II) is further described by formula (IIa):

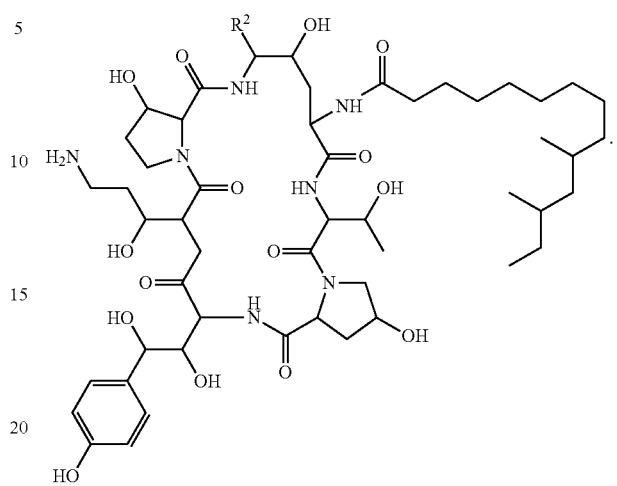

(IIa)

In formula (IIa), $R^2$ is $NH(CH_2CH_2O)_sCH_2CH_2X_8$, $NH(CH_2CH_2CH_2O)_sCH_2CH_2X_8$, $NH(CH_2CH_2NH)_tCH_2CH_2X_9$, $NH[CH_2(CH_2)_aO]_bCH\{CH_2[OCH_2(CH_2)_c]_dX_9\}_2$, $O[CH_2(CH_2)_aO]_bCH\{CH_2[OCH_2(CH_2)_c]_dX_9\}_2$, $NHCH_2(CH_2)_uX_{10}$, or $OCH_2(CH_2)_wX_{10}$; $X_8$ is OH, $OR^{G1}$, $NH_2$, $NHR^{G1}$, $NR^{G1}R^{G2}$, or $NR^{G1}R^{G2}R^{G3}$; each $X_9$ is, independently, selected from OH, $OR^{H1}$, $NHR^{H1}$, $NR^{H1}R^{H2}$, and $NR^{H1}R^{H2}R^{H3}$; $X_{10}$ is selected from $NR^{J1}R^{J2}R^{J3}$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); s is an integer from 1 to 5 (e.g., 1, 2, 3, 4, or 5); t is an integer from 1 to 5 (e.g., 1, 2, 3, 4, or 5); u is an integer from 1 to 3 (e.g., 1, 2, or 3); and each of $R^{G1}$, $R^{G2}$, $R^{G3}$, $R^{H1}$, $R^{H2}$, $R^{H3}$, $R^{J1}$, $R^{J2}$, and $R^{J3}$ is, independently, selected from $CH_3$, $CH_2CH_3$, $CH_2CH_2CH_3$, and $CH(CH_3)_2$, or a pharmaceutically acceptable salt thereof. In particular embodiments of the compounds of formula (II) and (IIa), one of $X_8$ and $X_9$ is selected from $N(CH_3)_3^+$ and $N(CH_2CH_3)_3^+$. In certain embodiments of the compounds of formula (II) and (IIa), $R^2$ is $NHCH[CH_2CH_2N(CH_3)_3^+]_2$, $NHCH_2CH_2OCH[CH_2CH_2N(CH_3)_3^+]_2$, or $NHCH_2CH_2OCH[CH_2CH_2N(CH_3)_3^+][CH_2CH_2OCH_2CH_2OH]$.

In still other embodiments, the compound of formula (I) is further described by formula (IIb):

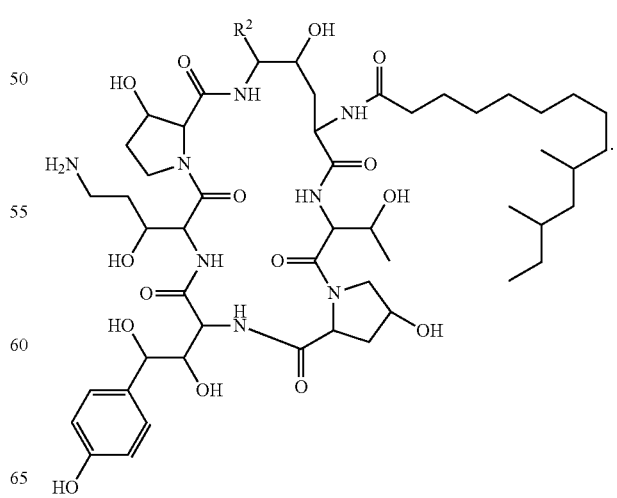

(IIb)

In formula (IIb), $R^2$ is $NH(CH_2CH_2O)_sCH_2CH_2X_8$, $NH(CH_2CH_2CH_2O)_sCH_2CH_2X_8$, $NH(CH_2CH_2NH)_tCH_2CH_2X_9$, $NH[CH_2(CH_2)_aO]_bCH\{CH_2[OCH_2(CH_2)_c]_dX_9\}_2$, $O[CH_2(CH_2)_aO]_bCH\{CH_2[OCH_2(CH_2)_c]_dX_9\}_2$, $NHCH_2(CH_2)_uX_{10}$, or $OCH_2(CH_2)_uX_{10}$; $X_8$ is $OCH_2(CH_2)_wZ_2$ or $NHCH_2(CH_2)_vZ_2$; each $X_5$ is, independently, selected from $OCH_2(CH_2)_wZ_2$ and $NHCH_2(CH_2)_vZ_2$; $X_{10}$ is $Z_2$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); s is an integer from 1 to 5 (e.g., 1, 2, 3, 4, or 5); t is an integer from 1 to 5 (e.g., 1, 2, 3, 4, or 5); u is an integer from 1 to 3 (e.g., 1, 2, or 3); w is an integer from 1 to 3 (e.g., 1, 2, or 3); $Z_2$ is selected from

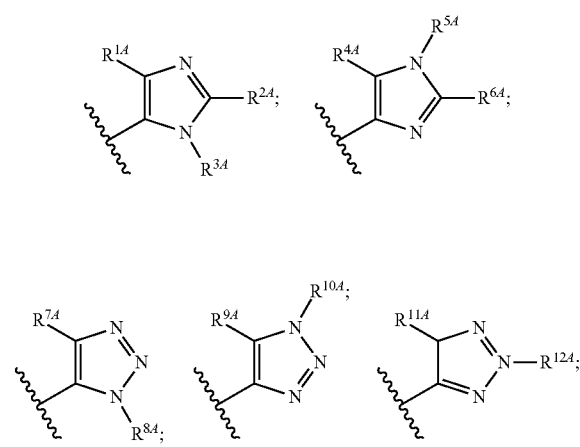

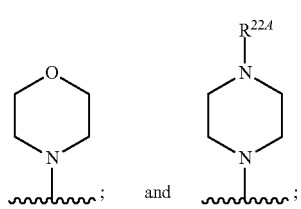

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof.

In one particular embodiment of the compounds of formula (II), (IIa), and (IIb), the compound is further described by one of the formulas:

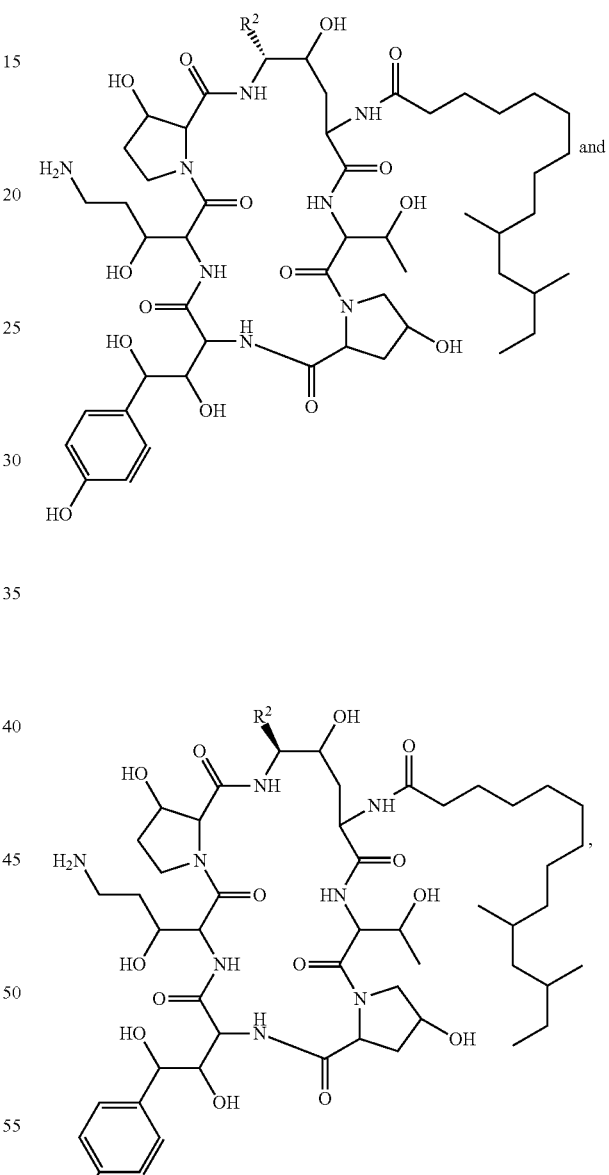

wherein $R^2$ is as described above.

The invention also features compounds described by formula (III):

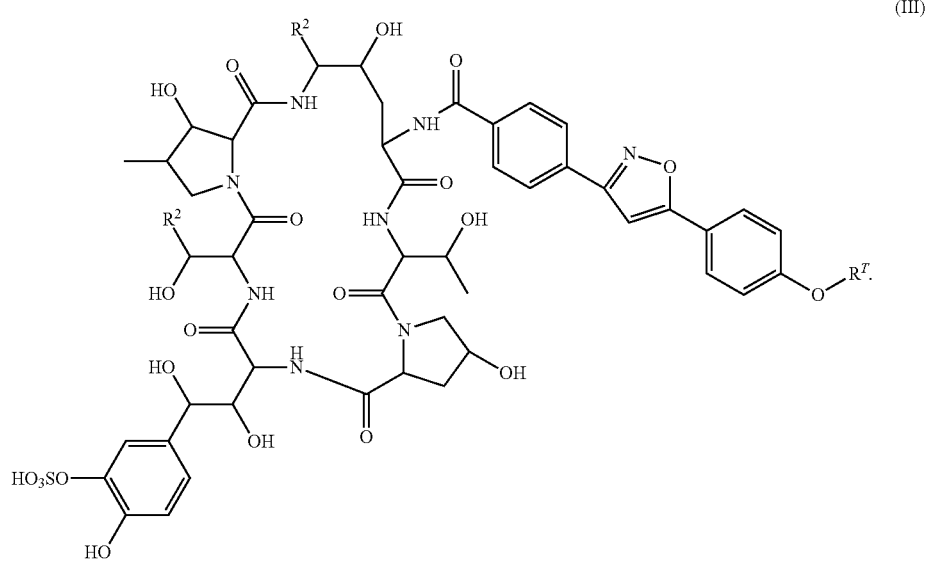

(III)

In formula (III), $R^1$ is $O(CH_2CH_2O)_nCH_2CH_2X_1$, $O(CH_2CH_2CH_2O)_nCH_2CH_2X_1$, $NHCH_2CH_2X_2$, $NH(CH_2CH_2O)_mCH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_pCH_2CH_2X_3$, $NHCH_2CH_2X_4$, $NH[CH_2(CH_2)_aO]_bCH\{CH_2[OCH_2(CH_2)_c]_dX_5\}_2$, $O[CH_2(CH_2)_aO]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$; $R^2$ is H, $CH_3$, $CH_2CH_2NH_2$, or $CH_2C(O)NH_2$; $R^T$ is n-pentyl, sec-pentyl, or iso-pentyl; $X_1$ is $NH_2$, $NHR^{A1}$, $NR^{A1}R^{A2}$, $NR^{A1}R^{A2}R^{A3}$, or $NHCH_2(CH_2)_vZ_1$; $X_2$ is OH, $OR^{B1}$, or $OCH_2(CH_2)_vZ_1$; $X_3$ is $NH_2$, $NHR^{C1}$, $NR^{C1}R^{C2}$, or $NR^{C1}R^{C2}R^{C3}$, or $NHCH_2(CH_2)_vZ_1$; $X_4$ is $NR^{D1}R^{D2}R^{D3}$ or $NHCH_2(CH_2)_vZ_1$; each $X_5$ is, independently, selected from OH, $OR^{E1}$, $NH_2$, $NHR^{E1}$, $NR^{E1}R^{E2}$, $NR^{E1}R^{E2}R^{E3}$, $OCH_2(CH_2)_vZ_1$, and $NHCH_2(CH_2)_vZ_1$; $X_6$ is selected from $NR^{F1}R^{F2}R^{F3}$ or $Z_1$; a is an integer from 1 to 2; b is an integer from 0 to 3 (e.g., 0, 1, 2, or 3); c is an integer from 1 to 2; d is an integer from 0 to 3 (e.g., 0, 1, 2, or 3); n is an integer from 1 to 5 (e.g., 1, 2, 3, 4, or 5); m is an integer from 1 to 5 (e.g., 1, 2, 3, 4, or 5); p is an integer from 1 to 5 (e.g., 1, 2, 3, 4, or 5); r is an integer from 1 to 5 (e.g., 1, 2, 3, 4, or 5); q is an integer from 1 to 3 (e.g., 1, 2, or 3); v is an integer from 1 to 3 (e.g., 1, 2, or 3); each of $R^{A1}$, $R^{A2}$, $R^{A3}$, $R^{B1}$, $R^{C1}$, $R^{C2}$, $R^{C3}$, $R^{D1}$, $R^{D2}$, $R^{D3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, and $CH(CH_3)_2$; $Z_1$ is selected from:

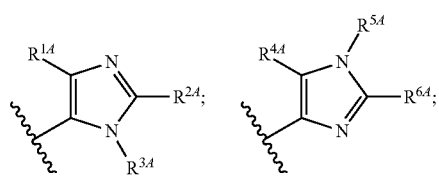

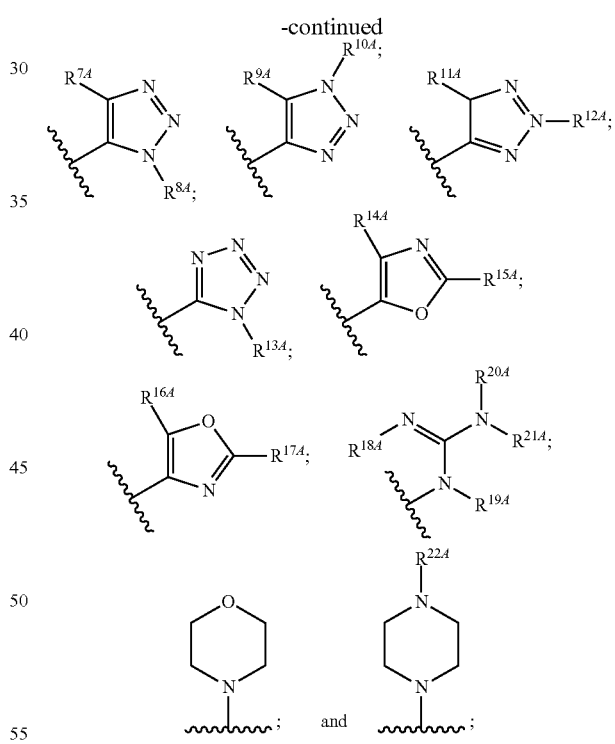

and each of $R^{1A}$, $R^{2A}$, $R^{3A}$, $R^{4A}$, $R^{5A}$, $R^{6A}$, $R^{7A}$, $R^{8A}$, $R^{9A}$, $R^{10A}$, $R^{11A}$, $R^{12A}$, $R^{13A}$, $R^{14A}$, $R^{15A}$, $R^{16A}$, $R^{17A}$, $R^{18A}$, $R^{19A}$, $R^{20A}$, $R^{21A}$, and $R^{22A}$ is, independently, selected from H, $CH_3$, $CH_2CH_3$, $CH_2CH_2CH_3$, and $CH(CH_3)_2$, or a pharmaceutically acceptable salt thereof. In particular embodiments of the compounds of formula (III), one of $X_1$, $X_3$, $X_4$, $X_5$, and $X_6$ is selected from $N(CH_3)_3^+$ and $N(CH_2CH_3)_3^+$.

In one particular embodiment of the compounds of formula (III), the compound is further described by one of the formulas:

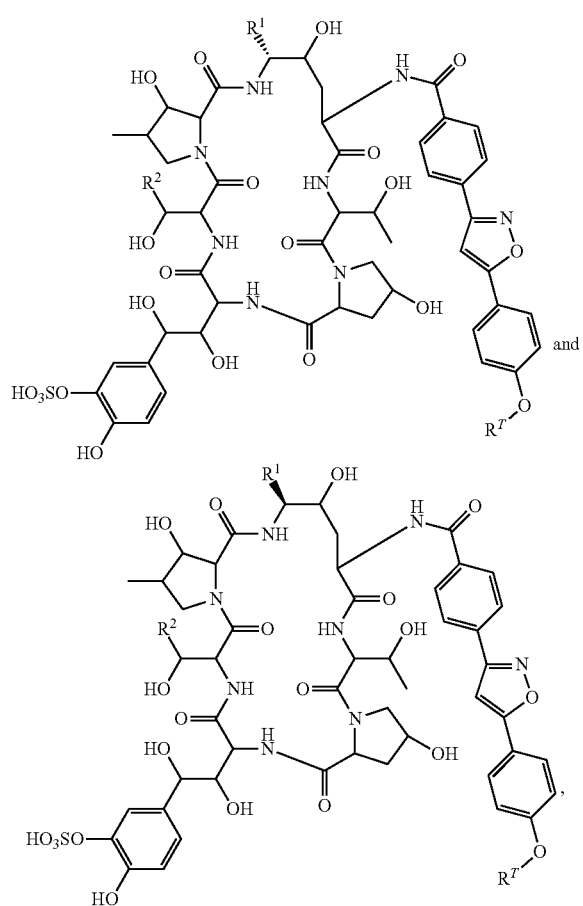

and wherein $R^1$ and $R^T$ are as described above.

The compounds of the invention include, without limitation, compound 1, compound 2, compound 3, compound 4, compound 5, compound 6, compound 7, compound 8, compound 9, compound 10, compound 11, compound 12, compound 13, compound 14, compound 16, compound 17, compound 18, compound 19, compound 20, compound 21, compound 22, and salts thereof.

The compounds of the invention can increased amphiphilicity; increased aqueous solubility (e.g., in 0.1M acetate buffer at pH 5.6); an increased therapeutic index; an increased elimination half-life; and/or an increased volume of distribution.

The invention also features a pharmaceutical composition including a compound of the invention, or a pharmaceutically acceptable salt thereof, and a pharmaceutically acceptable excipient. In particular embodiments, the pharmaceutical composition includes an acetate salt or a chloride salt of a compound of the invention.

The pharmaceutical compositions of the invention can be formulated for intravenous, topical, or oral administration in unit dosage form, or any other dosage form described herein.

The invention further features a method of treating a fungal infection in a subject by administering to the subject a pharmaceutical composition of the invention in an amount sufficient to treat the infection. In particular embodiments, the pharmaceutical composition is administered intravenously or topically. The pharmaceutical composition can be administered to treat a blood stream infection, tissue infection (e.g., lung, kidney, or liver infection) in the subject, or any other type of infection described herein. The fungal infection being treated can be an infection selected from tinea capitis, tinea corporis, tinea pedis, onychomycosis, perionychomycosis, pityriasis versicolor, oral thrush, vaginal candidosis, respiratory tract candidosis, biliary candidosis, eosophageal candidosis, urinary tract candidosis, systemic candidosis, mucocutaneous candidosis, aspergillosis, mucormycosis, paracoccidioidomycosis, North American blastomycosis, histoplasmosis, coccidioidomycosis, sporotrichosis, fungal sinusitis, or chronic sinusitis. In certain embodiments, the infection being treated is an infection by *Candida albicans, C. parapsilosis, C. glabrata, C. guilliermondii, C. krusei, C. lusitaniae, C. tropicalis, Aspergillus fumigatus, A. flavus, A. terreus. A. niger, A. candidus, A. clavatus,* or *A. ochraceus*.

The invention features a method of preventing a fungal infection in a subject by administering to the subject a pharmaceutical composition of the invention in an amount sufficient to prevent the infection. In particular embodiments, the pharmaceutical composition is administered intravenously at least once over a period of 1-30 days (e.g., 1, 2, 3, 4, or 5 times over a period of 1-30 days). For example, the methods of the invention can be used for prophylaxis treatment in subjects being prepared for an invasive medical procedure (e.g., preparing for surgery, such as receiving a transplant, stem cell therapy, a graft, a prosthesis, receiving long-term or frequent intravenous catheterization, or receiving treatment in an intensive care unit), in immunocompromised subjects (e.g., subjects with cancer, with HIV/AIDS, or taking immunosuppressive agents), or in subjects undergoing long term antibiotic therapy.

In one particular embodiment of any of the methods of the invention, the pharmaceutical composition includes compound 1, or any other compound described herein, or a pharmaceutically acceptable salt thereof.

The invention also features a method of preventing, stabilizing, or inhibiting the growth of fungi, or killing fungi by contacting the fungi or a site susceptible to fungal growth with a compound of the invention, or a pharmaceutically acceptable salt thereof.

As used herein, the terms "an amount sufficient" and "sufficient amount" refer to the amount of a drug required to treat or prevent an infection. The sufficient amount used to practice the invention for therapeutic or prophylactic treatment of conditions caused by or contributed to by an infection varies depending upon the manner of administration, the type of infection, the age, body weight, and general health of the subject. Ultimately, the attending physician or veterinarian will decide the appropriate amount and dosage regimen. Such amount is referred to as a "sufficient" amount.

By "fungal infection" is meant the invasion of a host by pathogenic fungi. For example, the infection may include the excessive growth of fungi that are normally present in or on the body of a subject or growth of fungi that are not normally present in or on a subject. More generally, a fungal infection can be any situation in which the presence of a fungal population(s) is damaging to a host body. Thus, a subject is "suffering" from a fungal infection when an excessive amount of a fungal population is present in or on the subject's body, or when the presence of a fungal population(s) is damaging the cells or other tissue of the subject.

By "increased amphiphilicity" is meant an increase in the solubility of a compound of the invention in both water (0.1M acetate buffer at pH 5.6) and glycerol in comparison to the parent echinocandin compound (i.e., compounds of formula (I), (Ia), and (Ib) can have an increased amphiphilicity in comparison to anidulafungin; compounds of formula (II), (IIa), and (IIb) can have an increased amphiphilicity in comparison to caspofungin; and compounds of formula (III) can have an increased amphiphilicity in comparison to micafungin).

By "increased elimination half-life" is meant an increase in the elimination half-life (e.g., as observed in a PK study as described in Example 24) for a compound of the invention in comparison to the parent echinocandin compound (i.e., compounds of formula (I), (Ia), and (Ib) can have an increased elimination half-life in comparison to anidulafungin; compounds of formula (II), (IIa), and (IIb) can have an increased elimination half-life in comparison to caspofungin; and compounds of formula (III) can have an increased elimination half-life in comparison to micafungin) administered under the same conditions (e.g., with the same carriers and other inactive excipients and by the same route). The compounds of the invention can exhibit at least 25%, 50%, 100%, 200%, or 300% longer elimination half-life than the corresponding parent echinocandin class compound.

By "increased volume of distribution" is meant an increase in the volume of distribution (e.g., as observed in a PK study as described in Example 24) for a compound of the invention in comparison to the parent echinocandin compound (i.e., compounds of formula (I), (Ia), and (Ib) can have an increased volume of distribution in comparison to anidulafungin; compounds of formula (II), (IIa), and (IIb) can have an increased volume of distribution in comparison to caspofungin; and compounds of formula (III) can have an increased volume of distribution in comparison to micafungin) administered under the same conditions (e.g., with the same carriers and other inactive excipients and by the same route). The compounds of the invention can exhibit at least 25%, 50%, 100%, 200%, or 300% greater volume of distribution than the corresponding parent echinocandin class compound.

By "increased therapeutic index" is meant an increase in the ratio of median lethal dose ($LD_{50}$) to median effective dose ($ED_{50}$) (e.g., as observed using a mouse model of infection) for a compound of the invention in comparison to the parent echinocandin compound (i.e., compounds of formula (I), (Ia), and (Ib) can have an increased therapeutic index in comparison to anidulafungin; compounds of formula (II), (IIa), and (IIb) can have an increased therapeutic index in comparison to caspofungin; and compounds of formula (III) can have an increased therapeutic index in comparison to micafungin) administered under the same conditions (e.g., with the same carriers and other inactive excipients and by the same route). The compounds of the invention can exhibit at least 25%, 50%, 100%, 200%, or 300% greater therapeutic index than the corresponding parent echinocandin class compound. For example, the compounds of the invention can exhibit extended circulating half-lives in vivo, allowing similar efficacy to be achieved at lower doses for the compound of the invention in comparison to the parent echinocandin compound.

As used herein, the term "treating" refers to administering a pharmaceutical composition for prophylactic and/or therapeutic purposes. To "prevent disease" refers to prophylactic treatment of a subject who is not yet ill, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

The term "unit dosage form" refers to physically discrete units suitable as unitary dosages, such as a pill, tablet, caplet, hard capsule or soft capsule, each unit containing a predetermined quantity of a drug. By "hard capsule" is meant a capsule that includes a membrane that forms a two-part, capsule-shaped, container capable of carrying a solid or liquid payload of drug and excipients. By "soft capsule" is meant a capsule molded into a single container carrying a liquid or semisolid payload of drug and excipients.

Other features and advantages of the invention will be apparent from the following detailed description, the drawings, and the claims.

DRAWINGS

FIG. 1 is a table of MEC and MIC values versus *Aspergillus* spp. obtained using methods described in Example 25.

FIG. 2 is a table of MIC values versus *Candida* spp. at 24 and 48 hours obtained using methods described in Example 26.

DETAILED DESCRIPTION

Figure 3A:
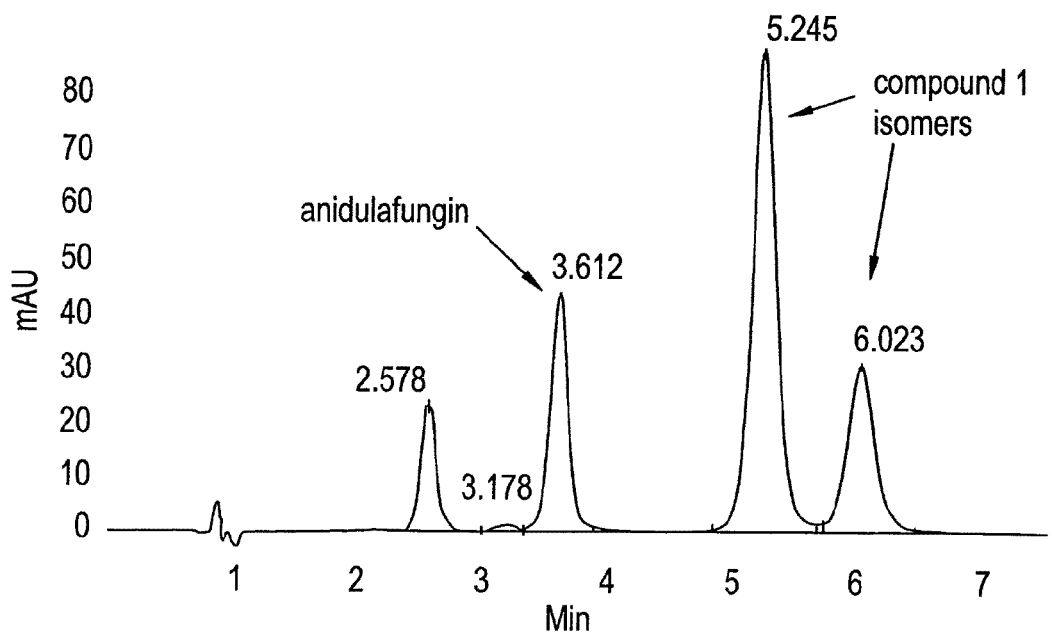
FIGS. 3A and 3B are reverse phase HPLC chromatograms of a mixture of anidulafungin and compound 1 isomers (FIG. 3A) and a purified sample of compound 1 (FIG. 3B). The chromatograms were obtained using the method described in Example 30.

The invention features echinocandin class compounds that have been modified such that they can exhibit (i) activity against one or more fungal species or genera; (ii) increased aqueous solubility and/or amphiphilicity; (iii) have an increased therapeutic index; (iv) suitability for topical administration; (v) suitability for intravenous administration; (vi) have an increased volume of distribution; and/or (vii) have an increased elimination half-life.

Synthesis

The compounds of the invention include compounds of formulas (I), (II), and (III). These compounds can be synthesized, for example, as described in the examples by coupling functionalized or unfunctionalized echinocandin class compounds with the appropriate acyl, alkyl, hydroxyl, and/or amino groups under standard reaction conditions.

Typically, the semi-synthetic echinocandin class compounds of the invention can be made by modifying the naturally occurring echinocandin scaffold. For example, pneumocandin $B_0$ is prepared by fermentation reactions; where fermentation and mixed broths produce a mixture of products which are then separated to produce pneumocandin $B_0$, which is used in the synthesis of caspofungin (see U.S. Pat. No. 6,610,822, which describes extraction of the echinocandin class compounds, such as, pneumocandin $B_0$, WF 11899 and echinocandin B by performing several extraction processes; and see U.S. Pat. No. 6,610,822, which describes methods for purifying the crude extracts).

For semi-synthetic approaches to compounds of the invention, the stereochemistry of the compound will be dictated by the starting material. Thus, the stereochemistry of the unnatural echinocandin derivatives will typically have the same stereochemistry as the naturally occurring echinocandin scaffold (representative stereochemistry is depicted in the examples) from which they are derived. Accordingly, any of the compounds shown below anidulafungin, caspofungin, or micafungin can be used as a starting material in the synthesis of the compounds of the invention which share the same stereochemical configuration at each of the amino acid residues found in the naturally occurring compound.

Accordingly, the echinocandin class compounds of the invention can be derived from the cyclic peptide antifungals which are produced by culturing various microorganisms.

The compounds of the invention can be synthesized, for example, using the methods described in the examples.

The compounds of the invention can also be used as starting materials in the synthesis of the compounds of formula (Ib) and (IIb). For example, amine-terminating compounds can be used to prepare guanidine derivatives. The conversion of amino groups to guanidine groups can be accomplished using standard synthetic protocols. For example, Mosher has described a general method for preparing mono-substituted guanidines by reaction of aminoiminomethanesulfonic acid with amines (Kim, K.; Lin, Y.-T.; Mosher, H. S. *Tetrahedron Lett.* 29: 3183, 1988). A more convenient method for guanylation of primary and secondary amines was developed by Bernatowicz employing 1H-pyrazole-1-carboxamidine hydrochloride; 1-H-pyrazole-1-(N,N'-bis(tert-butoxycarbonyl)carboxamidine; or 1-H-pyrazole-1-(N,N'-bis(benzyloxycarbonyl)carboxamidine. These reagents react with amines to give mono-substituted guanidines (see Bernatowicz et al., *J. Org. Chem.* 57: 2497, 1992; and Bernatowicz et al., *Tetrahedron Lett.* 34: 3389, 1993). In addition, Thioureas and S-alkyl-isothioureas have been shown to be useful intermediates in the syntheses of substituted guanidines (Poss et al., *Tetrahedron Lett.* 33: 5933 1992). The compounds of formula (Ib) and (IIb) that include a heterocyclic ring can be synthesized, for example, by coupling a hydroxyalkyl or aminoalkyl substituted heterocycle with a parent echinocandin compound using those coupling methods described in the examples.

Therapy and Formulation

The invention features compositions and methods for treating or preventing a disease or condition associated with a fungal infection (e.g., a yeast infection) by administering a compound of the invention. Compounds of the present invention may be administered by any appropriate route for treatment or prevention of a disease or condition associated with a fungal infection. These may be administered to humans, domestic pets, livestock, or other animals with a pharmaceutically acceptable diluent, carrier, or excipient. When administered orally, these may be in unit dosage form, or in as a liquid oral dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration formulations in the form of tablets or capsules, syrups, or oral liquid dosage forms; intranasal formulations, in the form of powders, nasal drops; formulated as ear drops; as formulated as aerosols, or formulated for topical administration, such as a cream or ointment.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The compound or combination may be optionally administered as a pharmaceutically acceptable salt, such as acid addition salts; metal salts formed by the replacement of an acidic proton with a metal, such as an alkali or alkaline earth salts (e.g., sodium, lithium, potassium, magnesium, or calcium salts); or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids; polymeric acids such as tannic acid, and carboxymethyl cellulose; and inorganic acid such as hydrochloric acid, hydrobromic acid, sulfuric acid, phosphoric acid. Metal complexes include zinc, and iron, among others.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc). Formulations for oral use may also be provided in unit dosage form as chewable tablets, tablets, caplets, or capsules (i.e., as hard gelatin capsules wherein the active ingredient is mixed with an inert solid diluent, or as soft gelatin capsules wherein the active ingredient is mixed with water or an oil medium).

The compounds of the invention can be formulated with excipients that improve the oral bioavailability of the compound. For example, the compounds of the invention can be formulated for oral administration with medium chain (C8 to C12) fatty acids (or a pharmaceutically acceptable salt thereof), such as capric acid, caprylic acid, lauric acid, or a pharmaceutically acceptable salt thereof, or a mixture thereof. The formulation can optionally include a medium chain (C8 to C12) alkyl alcohol, among other excipients. Alternatively, the compounds of the invention can be formulated for oral administration with one or more medium chain alkyl saccharides (e.g., alkyl (C8 to C14) beta-D-maltosides, alkyl (C8 to C14) beta-D-Gulcosides, octyl beta-D-maltoside, octyl beta-D-maltopyranoside, decyl beta-D-maltoside, tetradecyl beta-D-maltoside, octyl beta-D-glucoside, octyl beta-D-glucopyranoside, decyl beta-D-glucoside, dodecyl beta-D-glucoside, tetradecyl beta-D-glucoside) and/or medium chain sugar esters (e.g., sucrose monocaprate, sucrose monocaprylate, sucrose monolaurate and sucrose monotetradecanoate).

The formulations can be administered to human subjects in therapeutically effective amounts. Typical dose ranges are from about 0.01 µg/kg to about 800 mg/kg, or about 0.1 mg/kg to about 50 mg/kg, of body weight per day. The preferred dosage of drug to be administered is likely to depend on such variables as the type and extent of the disorder, the overall health status of the particular subject, the specific compound being administered, the excipients used to formulate the compound, and its route of administration.

The compounds of the invention can be used to treat, for example, tinea capitis, tinea corporis, tinea pedis, onychomycosis, perionychomycosis, pityriasis versicolor, oral thrush, vaginal candidosis, respiratory tract candidosis, biliary candidosis, eosophageal candidosis, urinary tract candidosis, systemic candidosis, mucocutaneous candidosis, aspergillosis, mucormycosis, paracoccidioidomycosis, North American blastomycosis, histoplasmosis, coccidioidomycosis, sporotrichosis, fungal sinusitis, and chronic sinusitis.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Analytical HPLC was performed using the following column(s) and conditions: Phenomenex Luna C18(2), 5 μm, 100 Å, 2.0×150 mm, 1-99% CH$_3$CN (0.1% TFA) in H$_2$O (0.1% TFA)/15 min. Preparative HPLC was performed using the following column: Waters Nova-Pak HR C18, 6 μm, 60 Å, 19×300 mm, CH$_3$CN/H$_2$O various linear gradients and modifiers as necessary at 10 mL/min.

The following abbreviations are used in the examples below: min (minutes), hr (hours), mmol (millimole), mL (milliliter), μm (micron), Å (angstrom), THF (tetrahydrofuran), DMF (dimethylformamide), TLC (thin layer chromatography), TFA (trifluoroacetic acid), HPLC (high performance liquid chromatography), RP (reversed phase), DIEA (diisopropylethylamine), LC/MS (liquid chromatography/mass spectrometry), $T_R$ (retention time on HPLC), C (Celsius), and FMOC (fluorenylmethyloxycarbonyl).

Example 1

Synthesis of Compound 1

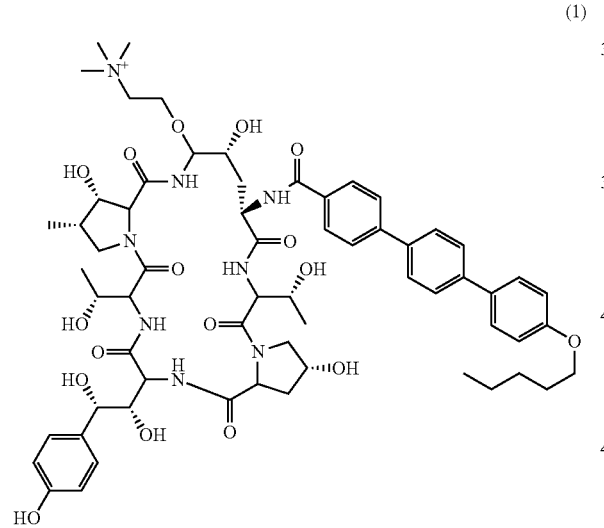

(1)

Anidulafungin (5 mg; 0.004 mmol) dissolved in anhydrous DMSO (0.2 mL) was treated choline chloride (13 mg; 0.093 mmol) and HCl (4M in 1,4-dioxane; 1.0 μL; 0.004 mmol). The resulting solution was stirred at room temperature for 2 days and heated at 40° C. for ~8 hr then diluted with water and acetonitrile and purified by preparative RP HPLC eluting with water (0.1% TFA)/CH$_3$CN (0.1% TFA). The product was isolated by freeze-drying to give 2.0 mg of compound 1 as a white solid. HPLC $T_R$ 10.84 min (90%). LC/MS, ESI+ m/z 1225.60 [M]$^+$.

Two alternative synthetic protocols are provided below.

Anidulafungin (3.00 g; 2.63 mmol) was suspended in dry THF (5 ml) and treated with phenylboronic acid (386 mg; 3.17 mol). The mixture was stirred until all solid dissolved (~30 min) then for an additional 30 min. THF was removed in vacuo at room temperature. The residue was again dissolved in THF and concentrated to dryness and then suspended in dry CH$_3$CN and concentrated to dryness to remove water. The resulting solid and N,N-dimethylethanolamine hydrochloride (9.25 g; 73.6 mmol) were mixed in dry DMSO (10 mL) until dissolved. The resulting clear viscous solution was treated with 4M HCl in dioxane (0.33 mL). The solution was stirred at room temperature for 3 days. The reaction was diluted with water (10 mL), and the resulting solution was then added slowly to a solution of sodium bicarbonate (12.4 g; 2 eq. vs. amine hydrochloride) in 300 ml water with vigorous stirring. The resulting flocculent precipitate was isolated by centrifuge. The solid was then triturated with 200 mL of water to give a translucent homogeneous suspension that was separated by centrifuge. The solids were dissolved in DMSO (15.0 mL) and treated with DIEA (0.460 ml; 2.64 mmol) was added followed by CH$_3$I (0.250 mL; 4.02 mmol), and the solution was stirred for 20 min at room temperature. Water (7 mL) was added followed by methanol (7 mL) and acetic acid (0.300 ml). The resulting solution was further diluted with water (7 mL) and purified by preparative RP HPLC eluting with CH3CN/aqueous 0.05M ammonium acetate pH 5.0. Fractions of interest were combined and concentrated in vacuo at 25° C. then freeze-dried to give 2.33 g of compound 1 as a white solid. HPLC $T_R$ 10.84 min (>98%). LC/MS, ESI+/− m/z 1225.60 [M]$^+$.

Anidulafungin (0.052 g; 0.046 mmol) was suspended in dry THF (~2 mL) and treated with phenylboronic acid (7 mg; 0.057 mol). The mixture was stirred until all solid dissolved (~30 min) and then for an additional 30 min. THF was removed in vacuo at room temperature. The residue was again dissolved in THF and concentrated to dryness and then suspended in dry CH$_3$CN and concentrated to dryness to remove water. The resulting solid at 0° C. was suspended in 20% TFA/CH$_3$CN (2.5 mL) and treated choline chloride (0.406 g; 2.9 mmol) and allowed to warm to room temperature. The solution was stirred at room temperature for 3 hr and then overnight at 5° C. The reaction was concentrated in vacuo at room temperature and then diluted with methanol and water and purified by preparative RP HPLC eluting with CH$_3$CN/aqueous 0.05M ammonium acetate pH 5.0. Fractions of interest were combined and concentrated in vacuo at 25° C. then freeze-dried to give 37 mg of compound 1 as a white solid. HPLC $T_R$ 10.84 min (98%). LC/MS, ESI+/− m/z 1225.60 [M]$^+$.

Example 2

Synthesis of Compound 2

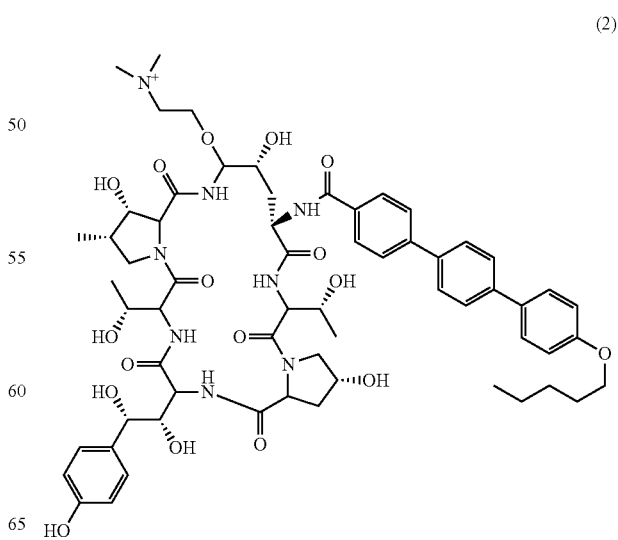

(2)

N,N-Dimethylethanolamine (9.9 μL; 0.100 mmol) in anhydrous DMF was treated with HCl (4M in 1,4-dioxane; 26.0 μL; 0.104 mmol). Anidulafungin (5 mg; 0.004 mmol) was added, and the resulting solution was stirred at room temperature for 1 day and heated at 40° C. for 3 days. The reaction was then diluted with water and acetonitrile and purified by preparative RP HPLC eluting with water (0.1% TFA)/CH$_3$CN (0.1% TFA). The product was isolated by freeze-drying to give 2.1 mg of compound 2 as a white solid. HPLC T$_R$ 10.94 min (86%). LC/MS, ESI+ m/z 1211.58 [M+H]$^+$.

Example 3

Synthesis of Compound 3

(3)

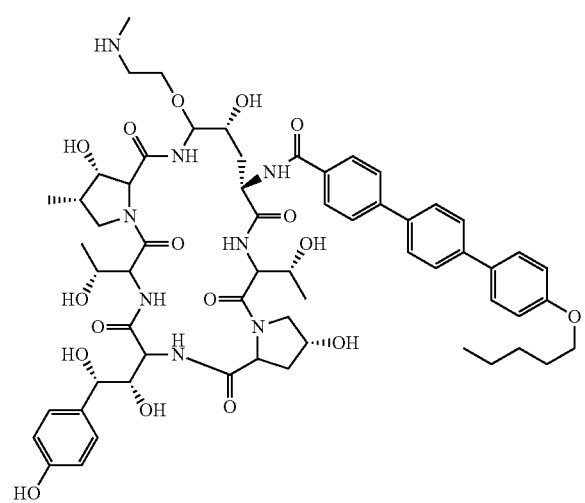

Anidulafungin (5 mg; 0.004 mmol) was mixed with N-methyl-2-aminoethanol hydrochloride (0.1 g; 0.9 mmol). Anhydrous DMSO (0.1 mL) was added, and the resulting solution was treated with HCl (4M in 1,4-dioxane; 1.0 μL; 0.004 mmol) and stirred at room temperature for 4 days. The reaction was then diluted with water and purified by preparative RP HPLC eluting with water (0.1% TFA)/CH$_3$CN (0.1% TFA). The product was isolated by freeze-drying to give 3.1 mg of compound 3 as a white solid. HPLC T$_R$ 10.98 min (98%). LC/MS, ESI+ m/z 1197.57 [M+H]$^+$.

Example 4

Synthesis of Compound 4

(4)

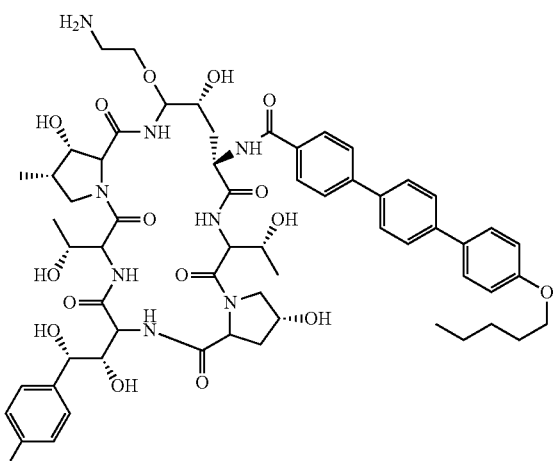

Ethanolamine (6.0 μL; 0.10 mmol) in anhydrous DMF was treated with HCl (4M in 1,4-dioxane; 26.0 μL; 0.104 mmol). Anidulafungin (6.4 mg; 0.0056 mmol) was added to give a clear solution which was stirred at room temperature for 16 days. The reaction was then diluted with water and acetonitrile and purified by preparative RP HPLC eluting with water (0.1% TFA)/CH$_3$CN (0.1% TFA). The product was isolated by freeze-drying to give 2.8 mg of compound 4 as a white solid. HPLC T$_R$ 10.90 min (95%). LC/MS, ESI+ m/z 1183.55 [M+H]$^+$.

Example 5

Synthesis of Compound 5

(5)

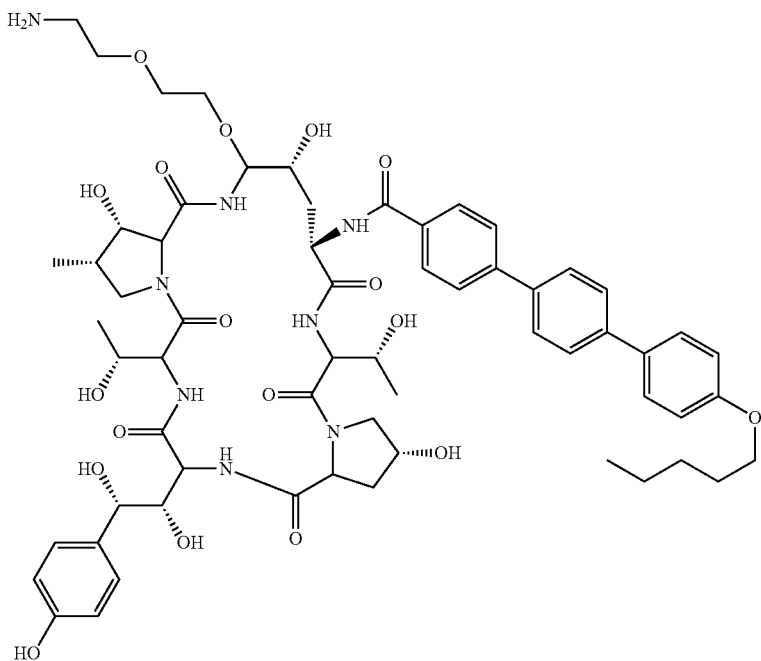

Anidulafungin (20 mg; 0.018 mmol) and 2-(2-aminoethoxy)ethanol hydrochloride (51 mg; 0.36 mmol) were dissolved in anhydrous DMSO (0.7 mL) and treated with HCl (4M in 1,4-dioxane; 4.0 μL; 0.016 mmol). The resulting solution was stirred at room temperature for 4 days then diluted with water and purified by preparative RP HPLC eluting with water (0.1% TFA)/CH$_3$CN (0.1% TFA). The product was isolated by freeze-drying to give 13 mg of compound 5 as a white solid. HPLC T$_R$ 10.82 min (>99%). LC/MS, ESI+/− m/z 1227.6 [M+H]$^+$, 1225.6 [M−H]$^-$.

Example 6

Synthesis of Compound 6

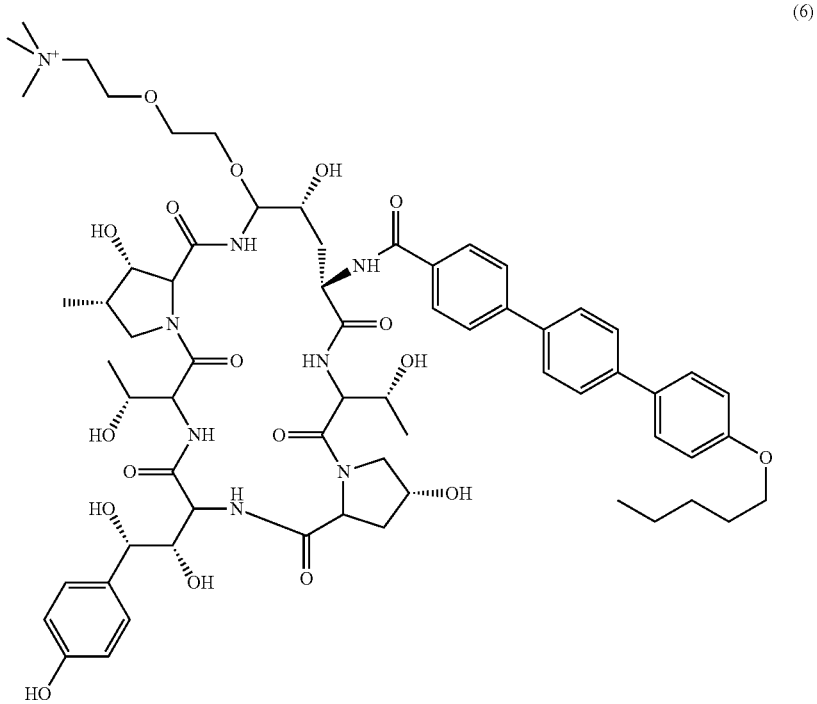 [SMILES: CCCCCOc1ccc(-c2ccc(-c3ccc(C(=O)N[C@H]4C[C@@H](O)C(OCCOCC[N+](C)(C)C)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CN5C(=O)C([C@@H](C)O)NC4=O)cc3)cc2)cc1]

(6)

2-(2-aminoethyoxy)-ethyl hemiaminal ether of anidulafungin trifluoroacetate (18 mg; 0.013 mmol) was dissolved in dry THF and concentrated to dryness at <30° C. The solid residue was taken up in DMSO and treated with DIEA (9 μL; 0.052 mmol) followed by CH$_3$I (2.5 μL; 0.040 mmol). The resulting solution was stirred overnight at room temperature then treated with additional CH$_3$I (1 μL; 0.016 mmol) and stirred for 2 hr longer. The solution was then diluted with water and methanol and purified by preparative RP HPLC eluting with water (0.1% TFA)/CH$_3$CN (0.1% TFA). The product was isolated by freeze-drying to give 9 mg of COMPOUND 6 as a white solid. HPLC T$_R$ 10.92 min (>99%). LC/MS, ESI+/− m/z 1269.6 [M]$^+$, 1267.6 [M−2H]$^-$.

Example 7

Synthesis of Compound 7

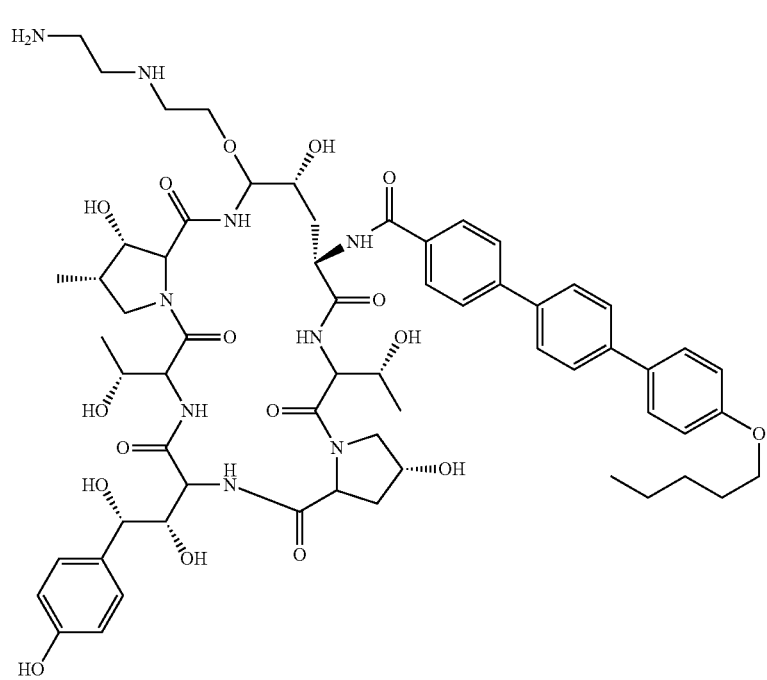

(7)

2-(2-aminoethyl)-aminoethanol (139 mg; 1.33 mmol) in 0.5 mL of DMSO was treated with HCl (4M in dioxane; 0.670 mL; 2.68 mmol) to give a bi-phasic mixture. Anidulafungin (35 mg; 0.031 mmol) was added followed by an additional 0.5 mL of DMSO. The mixture was heated to 40° C. to give a clear solution that was heated at 35° C. overnight. The solution was then diluted with water and methanol and purified by preparative RP HPLC eluting with water (0.1% TFA)/CH$_3$CN (0.1% TFA). The product was isolated by freeze-drying to give 11 mg of COMPOUND 7 as a white solid. HPLC T$_R$ 10.28 min (>95%). LC/MS, ESI+/− m/z 1226.6 [M]$^+$, 1224.6 [M−2H]$^-$.

Example 8

Synthesis of Compound 8

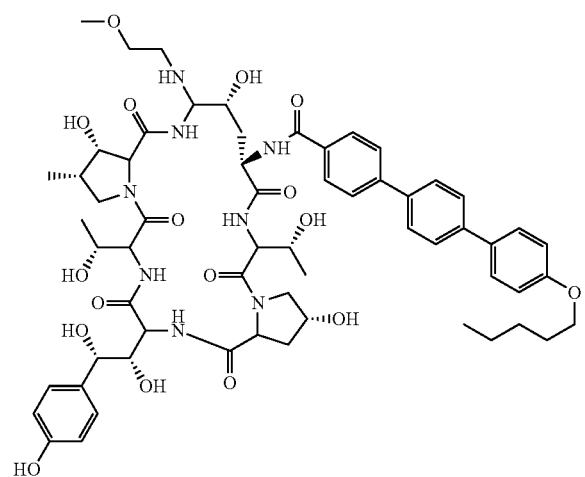

(8)

Anidulafungin (450 mg; 0.395 mmol) was twice suspended in acetonitrile (20 mL) and concentrated to dryness. The sample was then taken up in 20 mL of anhydrous THF and concentrated to ~10 mL. The solution under argon atmosphere was treated with phenylboronic acid (58 mg; 0.48 mmol) followed by activated 3 Å molecular sieves. The mixture was stirred slowly overnight then the supernatant was transferred to a dry flask with 2×5 mL THF rinses. The THF solution was concentrated to dryness the solid residue suspended in 40 mL of dry CH$_3$CN. The suspension was concentrated to 20 mL and under argon atmosphere cooled to −10° C. and treated with 4-methoxythiophenol (75 μL; 0.47 mmol) followed by TFA (2.4 mL). The resulting mixture was stirred at −15° C. overnight then, at −10° C., quenched by slow addition of water until flocculent precipitate developed. The mixture was stirred at 0° C. for 30 min then separated. Addition of water to the supernatant provided additional precipitate. The precipitates were dried in vacuo then combined and triturated with Et$_2$O. The solids were separated and triturated a second time with Et$_2$O. The isolated solids were then dried in vacuo overnight to give 393 mg of anidulafungin hemiaminal-(4-methoxy)phenylthioether as a white powder. HPLC T$_R$ 13.3 min (88%). LC/MS, ESI+/− m/z 1187.60 [M+H]$^+$, 1185.58 [M−H]$^-$.

Anidulafungin hemiaminal-(4-methoxy)phenylthioether (21 mg; 0.017 mmol) was dissolved in 0.1 mL of 1-methyl-2-aminoethanol to give a clear solution which was capped under argon and heated at 60° C. for 3 hr then stirred at room temperature overnight. The reaction was diluted with methanol, acidified by addition of TFA, further diluted with water, and purified by preparative RP HPLC eluting with CH$_3$CN/H$_2$O and 0.1% TFA. Purified product was isolated by freeze-drying to give 22 mg of compound 8 as a white solid. HPLC T$_R$ 11.15 min (84%). LC/MS, ESI+/− m/z 1197.57 [M+H]$^+$, 1219.55 [M+Na]+, 1195.56 [M−H]$^-$.

Example 9

Synthesis of Compound 9

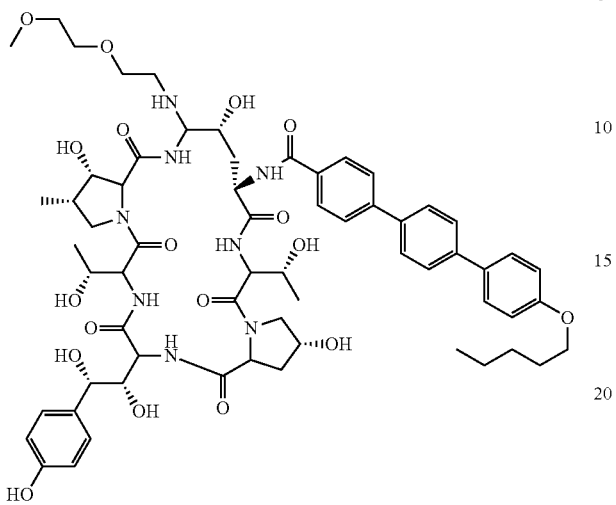

(9)

Anidulafungin hemiaminal-(4-methoxy)phenylthioether (20 mg; 0.016 mmol) was dissolved in 0.1 mL of 1-methyl-2-(2-aminoethyoxy)ethanol to give a clear solution which was capped under argon and heated at 60° C. for 8 hr then stirred at room temperature overnight. The reaction was diluted with methanol and water, acidified by addition of TFA, further diluted with water, and purified by preparative RP HPLC eluting with $CH_3CN/H_2O$ and 0.1% TFA. Purified product was isolated by freeze-drying to give 15 mg of compound 9 as a white solid. HPLC $T_R$ 11.18 min (86%). LC/MS, ESI+/−M/z 1241.60 $[M+H]^+$, 1239.59 $[M-H]^−$.

Example 10

Synthesis of Compound 10

Anidulafungin hemiaminal-(4-methoxy)phenylthioether (21 mg; 0.017 mmol) was dissolved in 0.1 mL of mPEG$_4$-NH$_2$ to give a clear solution which was capped under argon and heated at 50° C. overnight then at 65° C. for 2 hr. The reaction was diluted with methanol and water, acidified by addition of TFA, further diluted with water, and purified by preparative RP HPLC eluting with $CH_3CN/H_2O$ and 0.1% TFA. Purified product was isolated by freeze-drying to give 13 mg of compound 10 as a white solid. HPLC $T_R$ 11.26 min (88%). LC/MS, ESI+/− m/z 1329.65 $[M+H]^+$, 1351.63 $[M+Na]+$, 1327.64 $[M-H]^−$.

Example 11

Synthesis of Compounds 11

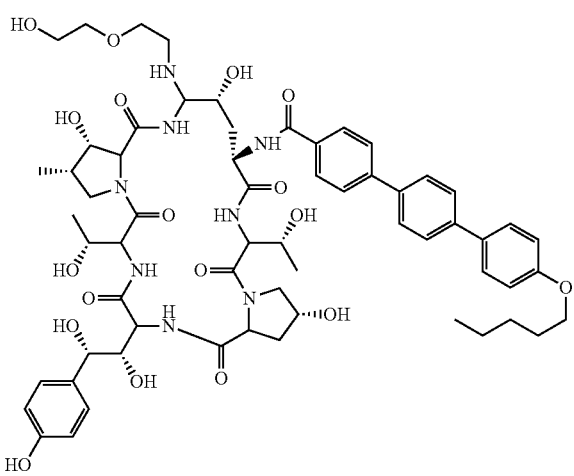

(11)

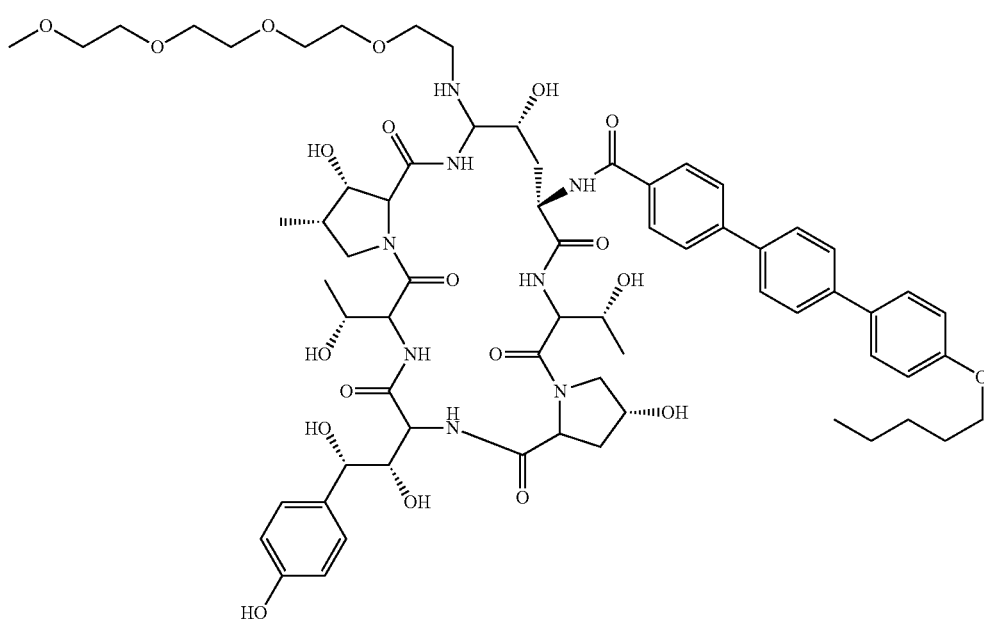

(10)

Anidulafungin hemiaminal-(4-methoxy)phenylthioether (20 mg; 0.016 mmol) was dissolved in 0.3 mL of 2-(2-aminoethyoxy)ethanol to give a clear solution which was capped under argon and stirred at room temperature overnight then heated at 60° C. for 1 hr. The reaction was diluted with methanol and water, acidified by addition of TFA, further diluted with water, and purified by preparative RP HPLC eluting with CH$_3$CN/H$_2$O and 0.1% TFA. Purified product was isolated by freeze-drying to give 15 mg of compound 11 as a white solid. HPLC T$_R$ 10.83 min (94%). LC/MS, ESI+/− m/z 1227.58 [M+H]$^+$, 1225.57 [M−H]$^−$.

Example 12

Synthesis of Compound 12

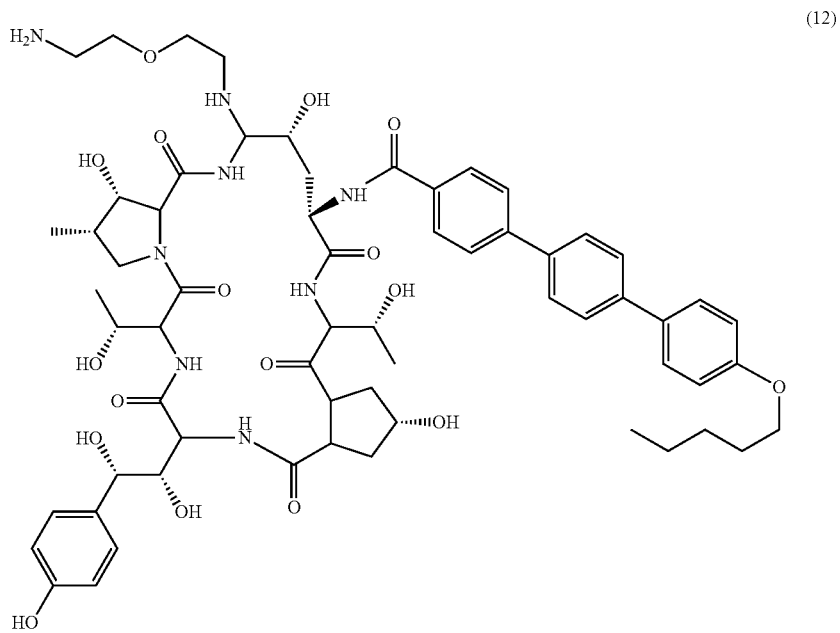 [SMILES: CCCCCOc1ccc(-c2ccc(-c3ccc(C(=O)N[C@H]4C[C@@H](O)C(NCCOCCN)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CC5C(=O)C([C@@H](C)O)NC4=O)cc3)cc2)cc1]

(12)

Anidulafungin hemiaminal-(4-methoxy)phenylthioether (19 mg; 0.015 mmol) was dissolved in 0.1 mL of 2-(2-aminoethyoxy)-ethylamine to give a clear solution which was capped under argon and heated at 60° C. for 1.5 hr. The reaction was diluted with methanol and water, acidified by addition of TFA, further diluted with water, and purified by preparative RP HPLC eluting with CH$_3$CN/H$_2$O and 0.1% TFA. Purified product was isolated by freeze-drying to give 11 mg of compound 12 as a white solid. HPLC T$_R$ 10.06 min (94%). LC/MS, ESI+/− m/z 1226.60 [M+H]$^+$, 1225.59 [M−H]$^−$.

Example 13

Synthesis of Compound 13

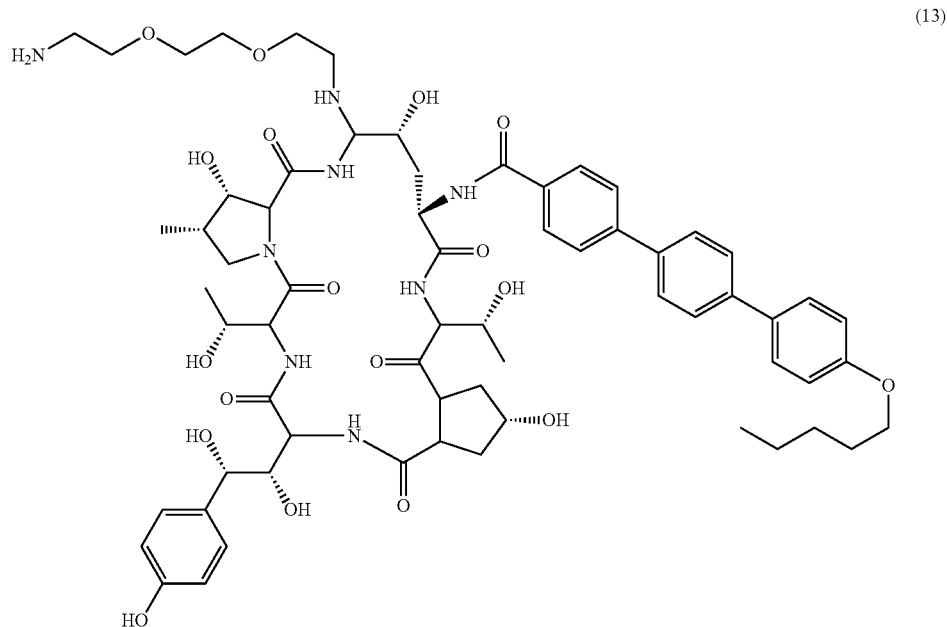 [SMILES: CCCCCOc1ccc(-c2ccc(-c3ccc(C(=O)N[C@H]4C[C@@H](O)C(NCCOCCOCCN)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CC5C(=O)C([C@@H](C)O)NC4=O)cc3)cc2)cc1]

(13)

Anidulafungin hemiaminal-(4-methoxy)phenylthioether (20 mg; 0.016 mmol) was dissolved in 0.1 mL of diamine to give a clear solution, which was capped under argon and heated at 60° C. for 1.5 hr and then allowed to stir at room temperature overnight. The reaction was diluted with methanol and water, acidified by addition of TFA, further diluted with water, and purified by preparative RP HPLC eluting with $CH_3CN/H_2O$ and 0.1% TFA. Purified product was isolated by freeze-drying to give 11 mg of compound 13 as a white solid. HPLC $T_R$ 10.06 min (92%). LC/MS, ESI+/− m/z 1270.62 $[M+H]^+$, 1268.61 $[M-H]^-$.

Example 14

Synthesis of Compound 14

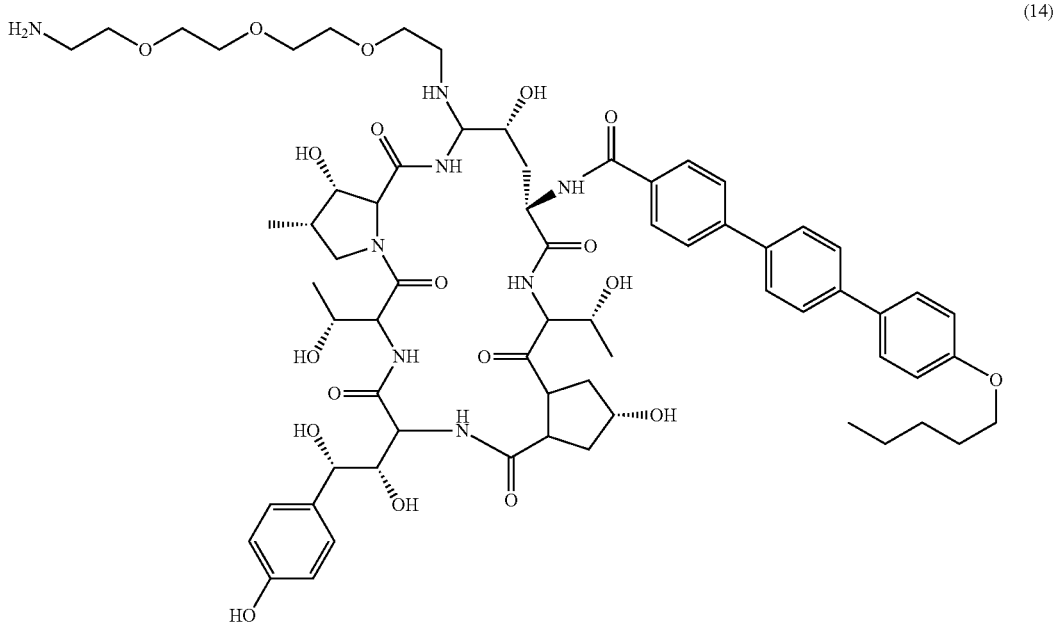 [SMILES: CCCCCOc1ccc(-c2ccc(-c3ccc(C(=O)N[C@H]4C[C@@H](O)C(NCCOCCOCCOCCN)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CC5C(=O)C([C@@H](C)O)NC4=O)cc3)cc2)cc1]

(14)

Anidulafungin hemiaminal-(4-methoxy)phenylthioether (21 mg; 0.017 mmol) was dissolved in 0.1 mL of mono-BOC-NH-PEG$_4$-NH$_2$ to give a clear solution which was capped under argon and heated at 50° C. until product:starting material ratio was ~1:1. The reaction was treated with TFA (4 mL), stirred at room temperature for ~30 min, concentrated in vacuo, then diluted with water, and purified by preparative RP HPLC eluting with CH$_3$CN/H$_2$O and 0.1% TFA. Purified product was isolated by freeze-drying to give 5 mg of compound 14 as a white solid. HPLC T$_R$ 10.13 min (76%). LC/MS, ESI+/− m/z 1314.65 [M+H]$^+$, 1312.64 [M−H]$^−$.

Example 15

Synthesis of Compound 15

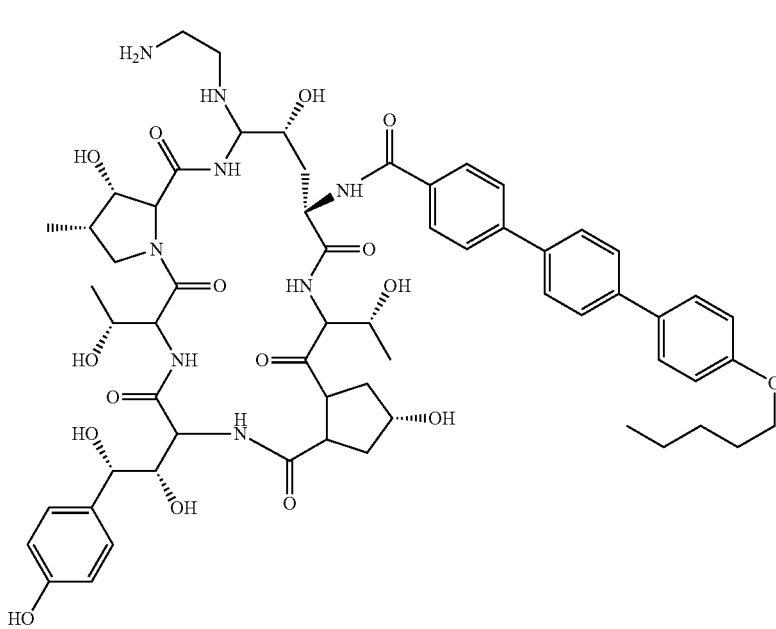

(15)

Anidulafungin hemiaminal-(4-methoxy)phenylthioether (49 mg; 0.039 mmol) suspended in 0.5 mL of CH$_3$CN at 0° C. was treated with 0.3 mL of ethylene diamine to give a clear solution which was allowed to come to room temperature and stirred for 4 hr. The solution was diluted with 0.5 mL of methanol and 2 mL of water and acidified with TFA. The solution was further diluted with 2 mL each of methanol and water then purified by preparative RP HPLC eluting with CH$_3$CN/H$_2$O and 0.1% TFA. Purified product was isolated by freeze-drying to give 30 mg of compound 15 as a white solid. HPLC T$_R$ 10.13 min (88%). LC/MS, ESI+/− m/z 1182.57 [M+H]$^+$, 1180.56 [M−H]$^−$.

Example 16
Synthesis of Compound 16

(16)

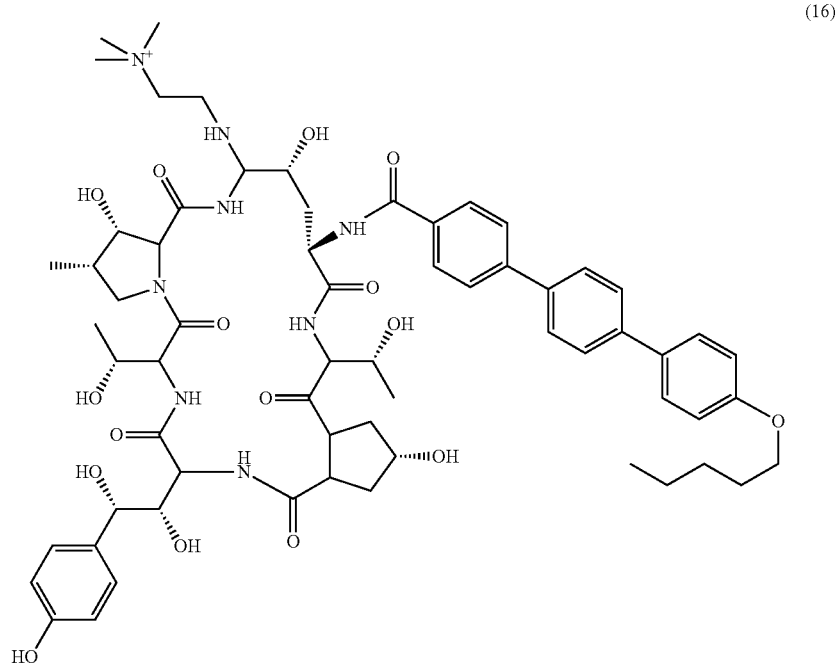 [SMILES: CCCCCOc1ccc(-c2ccc(-c3ccc(C(=O)N[C@H]4C[C@@H](O)C(NCC[N+](C)(C)C)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CC5C(=O)C([C@@H](C)O)NC4=O)cc3)cc2)cc1]

N,N-dimethylaminoethyl anidulafungin aminal: Anidulafungin hemiaminal-(4-methoxy)phenylthioether (150 mg; 0.119 mmol) was dissolved in 0.5 mL of N,N-dimethylethylene diamine to give a light yellow solution which was heated at 45° C. for 18 hours. The reaction was diluted with 80 mL of Et$_2$O to precipitate product. The collected solids were triturated with Et$_2$O then separated and dried in vacuo overnight to give 153 mg of N,N-dimethylaminoethyl anidulafungin animal as an off-white solid. HPLC T$_R$ 10.37 min (76%). LC/MS, ESI+/− m/z 1210.60 [M+H]$^+$, 1208.60 [M−H]$^−$.

N,N-dimethylaminoethyl anidulafungin aminal (153 mg; ≤0.119 mmol) in anhydrous DMSO was treated with CH$_3$I (8 μL; 0.129 mmol) and stirred at room temperature overnight. The reaction was treated with additional CH$_3$I (3 μL; 0.048 mmol) and DIEA (7 μL; 0.040 mmol) and stirred at room temp for an additional 2 hr longer. The reaction was acidified with ~5 μL of TFA, diluted with water and methanol, and purified by preparative RP HPLC eluting with CH$_3$CN/H$_2$O and 0.1% TFA. Purified product was isolated by freeze-drying to give 64 mg of compound 16 as a white solid. HPLC T$_R$ 10.36 min (92%). LC/MS, ESI+/− m/z 1224.61 [M]$^+$, 1222.61 [M−2H]$^−$, 1268.61 [M+formate]$^−$.

Example 17
Synthesis of Compound 17

(17)

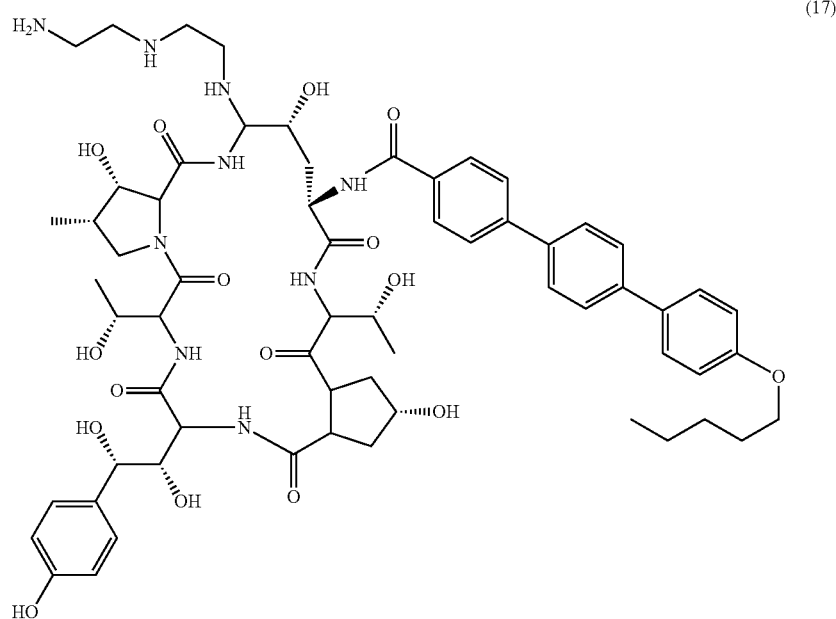

Anidulafungin hemiaminal-(4-methoxy)phenylthioether (82 mg; 0.065 mmol) was dissolved in 0.3 mL of diethylenetriamine to give a clear solution which was capped under argon and heated at 60° C. for 45 min. The cooled solution was diluted with diethyl ether to precipitate products and the supernatant was removed. The solids were concentrated in vacuo and then taken up in 1 mL of methanol and 1 mL of water and acidified with TFA. The resulting solution was purified by preparative RP HPLC eluting with $CH_3CN/H_2O$ and 0.1% TFA. Purified product was isolated by freeze-drying to give 44 mg of compound 17 as a white solid. HPLC $T_R$ 9.77 min (84%). LC/MS, ESI+/− m/z 1225.61 $[M+H]^+$, 1223.61 $[M−H]^-$.

Example 18

Synthesis of Compound 18

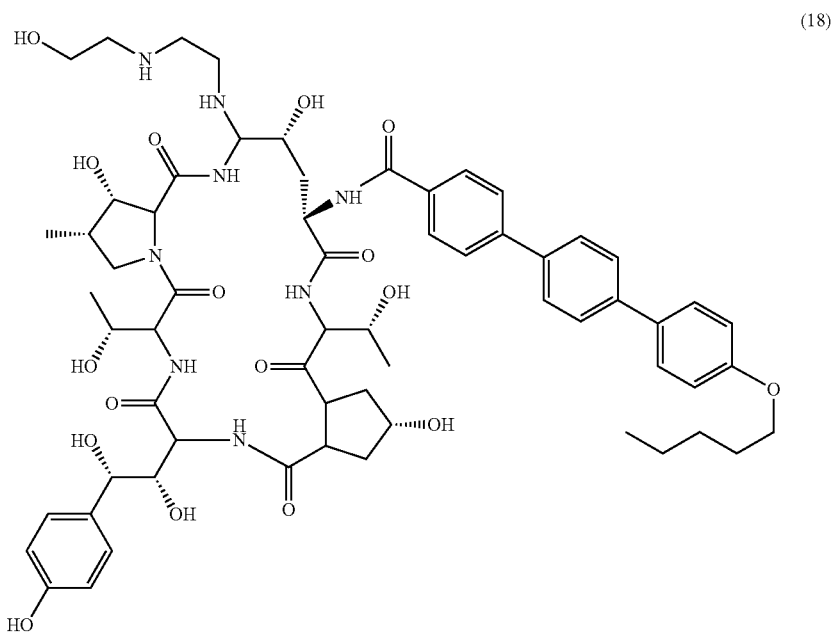 [SMILES: CCCCCOc1ccc(-c2ccc(-c3ccc(C(=O)N[C@H]4C[C@@H](O)C(NCCNCCO)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CC5C(=O)C([C@@H](C)O)NC4=O)cc3)cc2)cc1]

(18)

Anidulafungin hemiaminal-(4-methoxy)phenylthioether (19 mg; 0.015 mmol) was dissolved in 0.3 mL of N-(2-aminoethyl)-2-aminoethanol to give a clear solution which was capped under argon and stirred at room temperature overnight then heated at 60° C. for 1.5 hr. The reaction was diluted with methanol and water, acidified by addition of TFA, further diluted with water, and purified by preparative RP HPLC eluting with $CH_3CN/H_2O$ and 0.1% TFA. Purified product was isolated by freeze-drying to give 10 mg of compound 18 as a white solid. HPLC $T_R$ 10.09 min (90%). LC/MS, ESI+/− m/z 1226.60 $[M+H]^+$, 1225.59 $[M−H]^-$.

Example 19

Synthesis of Compound 19

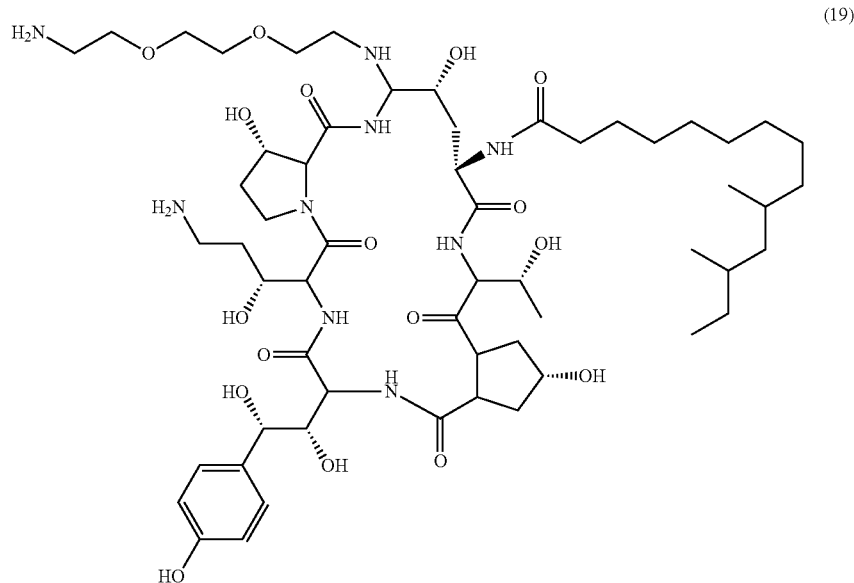 [SMILES: CCC(C)CC(C)CCCCCCCCC(=O)N[C@H]1C[C@@H](O)C(NCCOCCOCCN)NC(=O)C2[C@@H](O)CCN2C(=O)C([C@H](O)CCN)NC(=O)C([C@H](O)[C@@H](O)c2ccc(O)cc2)NC(=O)C2C[C@@H](O)CC2C(=O)C([C@@H](C)O)NC1=O]

(19)

Pneumocandin B₀ hemiaminal-(4-methoxy)phenylthioether: Pneumocandin B₀ (509 mg; 0.48 mmol) was twice suspended in CH₃CN (25 mL) and concentrated in vacuo at room temperature to remove water. The sample was then suspended in anhydrous THF (25 mL) and concentrated to dryness. The residue was taken up in anhydrous THF (25 mL) and concentrated at room temperature to 10 mL. The resulting suspension was treated with phenylboronic acid (69 mg; 0.57 mmol) and stirred at room temperature until all solid dissolved to give a slightly turbid solution. The solution was concentrated to dryness, and the remaining solid was suspended in CH₃CN (25 mL). The resulting suspension was concentrated to ~10 mL, cooled to −10° C. under dry argon, and treated with 4-methoxythiophenol (72 µL) followed by trifluoroacetic acid (1.4 mL) added dropwise. The mixture was stirred under argon at −15 to −20° C. for 2 days, then brought to 0° C. and treated with 25 mL of water added dropwise to give a white suspension which was stirred at 0° C. for 20 minutes then separated. The solids were triturated and re-suspended in 20 mL of 25% CH₃CN/H₂O then separated and dried in vacuo. The resulting solid was triturated with diethyl ether. The supernatant was removed, and the solids were dried in vacuo to give 430 mg of the title compound as a dense white powder. 89% purity by HPLC, UV det. at 216-224 nm; LC/MS ESI+/− m/z 1187.59 [M+H]⁺ (calculated 1187.59), 1185.58 [M−H]⁻ (calculated 1185.58), 1045.55 [M-MeOPhSH]⁻ (calculated 1045.55).

Pneumocandin B₀ hemiaminal-(4-methoxy)phenylthioether Amine: Pneumocandin B₀ hemiaminal-(4-methoxy)phenylthioether (533 mg; 0.45 mmol) suspended in anhydrous THF (15 mL) was treated with phenyl boronic acid (67 mg; 0.55 mmol) followed by 3 Å molecular sieves (~15 beads). The mixture under argon was stirred at room temperature overnight to give a clear solution which was concentrated to ~7 mL under dry argon stream in a vented flask. The solution was then transferred to a dry flask followed by 2 THF rinses of the molecular sieves to give a reaction volume of ~10 mL. The solution under argon was cooled to 0° C., treated with BH₃-DMS (2.0 M in THF; 1.4 mL; 2.8 mmol), and stirred at 0° C. After 2 hr, anhydrous THF (2 mL) was added to dissolve gel that had formed. This was followed by additional BH₃-DMS (0.5 mL; 1.0 mmol). The mixture was maintained at 0° C. for 1 hr longer, then stirred at room temperature for ~3 hr, then cooled to 0° C. and quenched by slow addition of 1M HCl (1.3 mL). The quenched reaction was stored at −20° C. overnight then concentrated to ~3 mL. The resulting mixture was diluted with methanol and water (~1:1) to 20 mL then purified by preparative RP HPLC eluting with 10-70% CH₃CN/H₂O (0.1% TFA). Fractions of interest were combined and freeze-dried to give 245 mg (42% TY) of the title compound as a bright white solid. 94% purity by HPLC, UV det. at 216-224 nm; LC/MS ESI+/− m/z 1173.61 [M+H]⁺ (calculated 1173.61), 1031.57 [M-MeOPhSH]⁻ (calculated 1031.57).

Pneumocandin hemiaminal-(4-methoxy)phenylthioether amine (20 mg; 0.016 mmol) was dissolved in 2,2'-(ethylenedioxy)bis(ethylamine) (0.1 mL). The solution was heated at 40° C. overnight and then at 60° C. for 1.5 hr and then diluted with methanol (0.5 mL) and water (2 mL) and acidified with TFA. The acidified mixture was further diluted with water and methanol then purified by preparative RP HPLC eluting with water (0.1% TFA)/CH₃CN (0.1% TFA). Product was isolated by freeze-drying to give 15 mg of compound 19 as a white solid. HPLC $T_R$ 9.22 min (99%). LC/MS, ESI+/− m/z 1181.70 [M+H]⁺, 1179.70 [M−H]⁻.

Example 20

Synthesis of Compound 20

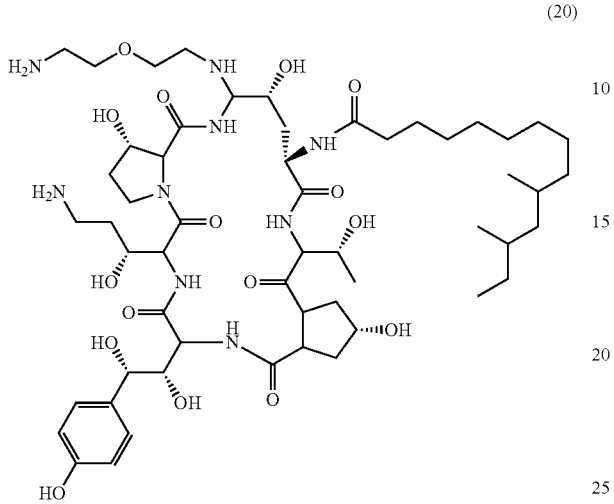

(20)

Pneumocandin hemiaminal-(4-methoxy)phenylthioether amine (17 mg; 0.013 mmol) was dissolved in 2,2'-oxobis(ethylamine) (0.1 mL). The solution was heated at 40° C. overnight and then diluted with methanol (0.5 mL) and water (2 mL) and acidified with TFA. The acidified mixture was further diluted with water and methanol and then purified by preparative RP HPLC eluting with water (0.1% TFA)/CH$_3$CN (0.1% TFA). Product was isolated by freeze-drying to give 12 mg of compound 20 as a white solid. HPLC T$_R$ 9.22 min (96.0%). LC/MS, ESI+/− m/z 1137.68 [M+H]$^+$, 1135.67 [M−H]$^-$.

Example 21

Synthesis of Compound 21

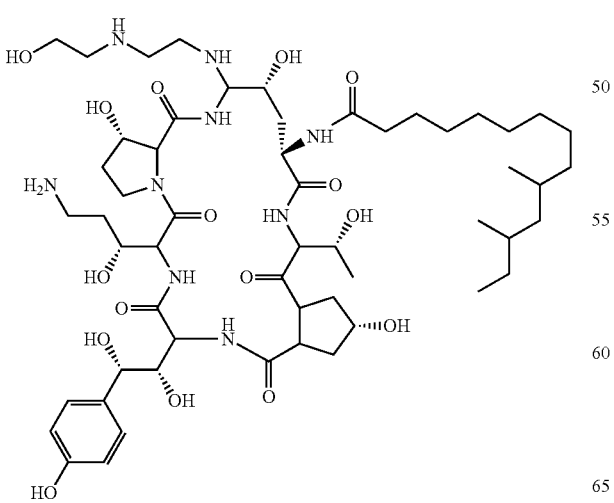

(21)

Pneumocandin hemiaminal-(4-methoxy)phenylthioether amine (19 mg; 0.015 mmol) was dissolved in 2-(aminoethylamino)ethanol (0.1 mL). The solution was heated at 60° C. for 2 hr and then diluted with methanol (0.5 mL) and water (2 mL) and acidified with TFA. The acidified mixture was further diluted with water and methanol and then purified by preparative RP HPLC eluting with water (0.1% TFA)/CH$_3$CN (0.1% TFA). Product was isolated by freeze-drying to give 11 mg of compound 21 as a white solid. HPLC T$_R$ 9.34 min (97.7%). LC/MS, ESI+/− m/z 1137.68 [M+H]$^+$, 1135.67 [M−H]$^-$.

Example 22

Synthesis of Compound 22

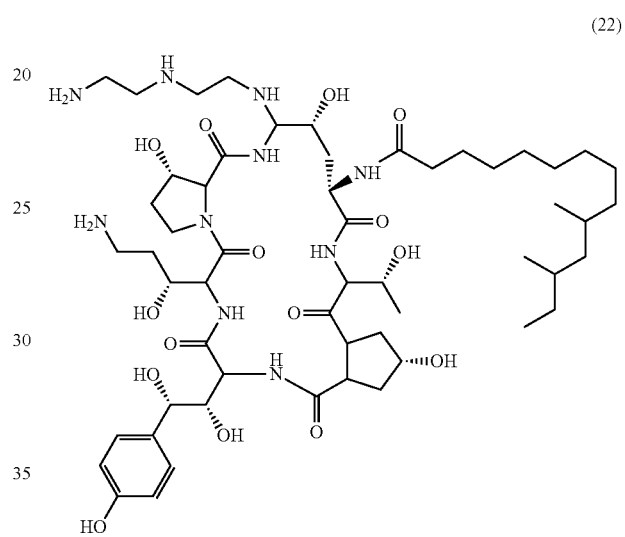

(22)

Pneumocandin hemiaminal-(4-methoxy)phenylthioether amine (19 mg; 0.015 mmol) was dissolved in 2-(aminoethylamino)ethanol (0.1 mL). The solution was stirred at room temperature for 1 hr, heated at 60° C. for 15 min, diluted with methanol (0.5 mL) and water (2 mL), and acidified with TFA. The acidified mixture was further diluted with water and methanol then purified by preparative RP HPLC eluting with water (0.1% TFA)/CH$_3$CN (0.1% TFA). Product was isolated by freeze-drying to give 13 mg of compound 22 as a white solid. HPLC T$_R$ 9.12 min (93.1%). LC/MS, ESI+/− m/z 1136.69 [M+H]$^+$, 1134.68 [M−H]$^-$.

Example 23

In Vivo Activity Following IP Administration

The objective of these studies was to evaluate the efficacy of test compounds in the mouse candidiasis infection model. Amounts of test articles are uncorrected.

Inoculum Preparation

The strain, *C. albicans* R303 was transferred from frozen storage onto Sabauroud dextrose agar (SDA) plates and grown for ~24 hr at 35° C. The inoculum was prepared by transferring colonies from the plate to phosphate buffered saline (PBS) and the concentration adjusted to approximately 10$^6$ CFU/mL with the aid of a spectrophotometer. The stock was diluted 1:9 to prepare the inoculum. Prior to each run the concentration was verified using the dilution plate count method.

Female CD-1 mice were used in this study. The animals were approximately seven-weeks-old at the start of the study and weighed about 15-30 g.

Mice were made neutropenic with IP injections of cyclophosphamide (150 mg/kg in 10 mL/kg) at 4 and 1 day before inoculation. Each animal was inoculated with the appropriate concentration by injecting 0.1 mL of inoculum into a tail vein. The test compounds were administered IP at 2 hr after infection.

In a typical procedure, the kidneys were collected from four mice in control group 1 (untreated) at 2 hr after infection, and from another four mice in control group 2 (untreated) at 24 hr after infection. Kidneys were removed aseptically from each mouse and were combined in a sterile tube. An aliquot (2 mL) of sterile PBS was added to each tube and the contents homogenized with a tissue homogenizer (Polytron 3100). Serial dilutions of the tissue homogenates were conducted and 0.1 mL aliquots were spread on SDA plates and the plates incubated at 35° C. overnight. The CFU/kidneys were determined from colony counts. Data were analyzed using one-way ANOVA with either the Tukey-Kramer Multiple Comparisons Test or Dunnett Test (GraphPad InStat version 3.06, GraphPad Software, San Diego, Calif.).

The data reported below are the average of four mice. Each run included a separate control and each is tabulated separately.

First Run

TABLE 1

| Treatment (IP administration, mg/kg) | Mean log$_{10}$ CFU/kidneys (±SD) | Difference from 24-h control |
|---|---|---|
| Infected control - 2 h | 3.27 ± 0.12 | |
| Infected control - 24 h | 5.20 ± 0.22 | |
| anidulafungin - 1 mg/kg | 3.37 ± 0.72 | −1.83 *** |
| compound 1 - 5 mg/kg | 0.40 ± 0.80 | −4.80 *** |
| compound 2 - 5 mg/kg | 1.60 ± 0.35 | −3.60 *** |
| compound 3 - 5 mg/kg | 1.57 ± 0.20 | −3.63 *** |
| compound 4 - 5 mg/kg | 0.73 ± 0.85 | −4.47 *** | ns, difference not significant;
*** significant at $P < 0.001$.

Second Run

TABLE 2

| Treatment (IP administration, mg/kg) | Mean log$_{10}$ CFU/kidneys (±SEM) | Difference from 24-h control |
|---|---|---|
| Infected control - 2 h | 2.92 ± 0.07 | |
| Infected control - 24 h | 4.87 ± 0.10 | |
| anidulafungin - 0.5 mg/kg | 4.41 ± 0.12 | −0.47 ns |
| anidulafungin - 1.5 mg/kg | 2.77 ± 0.20 | −2.11 *** |
| anidulafungin - 4.5 mg/kg | 1.10 ± 0.38 | −3.78 *** |
| compound 1 - 0.5 mg/kg | 2.80 ± 0.11 | −2.08 *** |
| compound 1 - 1.5 mg/kg | 1.83 ± 0.14 | −3.05 *** |
| compound 1 - 4.5 mg/kg | 0.98 ± 0.33 | −3.90 *** |
| compound 4 - 0.5 mg/kg | 3.38 ± 0.10 | −1.50 ** |
| compound 4 - 1.5 mg/kg | 0.65 ± 0.38 | −4.22 *** |
| compound 4 - 4.5 mg/kg | 0.65 ± 0.38 | −4.22 *** |
| compound 5 - 0.5 mg/kg | 3.65 ± 0.10 | −1.22 ns |
| compound 5 - 1.5 mg/kg | 0.73 ± 0.42 | −4.15 *** |
| compound 5 - 4.5 mg/kg | 0.00 ± 0.00 | −4.87 *** |
| compound 15 - 0.5 mg/kg | 1.25 ± 0.45 | −3.63 *** |
| compound 15 - 1.5 mg/kg | 0.96 ± 0.57 | −3.91 *** |
| compound 15 - 4.5 mg/kg | 0.73 ± 0.42 | −4.15 *** |
| compound 6 - 0.5 mg/kg | 4.75 ± 0.19 | −0.13 ns |

TABLE 2-continued

| Treatment (IP administration, mg/kg) | Mean log$_{10}$ CFU/kidneys (±SEM) | Difference from 24-h control |
|---|---|---|
| compound 6 - 1.5 mg/kg | 1.60 ± 0.17 | −3.27 *** |
| compound 6 - 4.5 mg/kg | 0.00 ± 0.00 | −4.87 *** | ns, difference not significant;
** significant at $P < 0.01$.
*** significant at $P < 0.001$.

Third Run

TABLE 3

| Treatment (IP administration, mg/kg) | Mean log$_{10}$ CFU/kidneys (±SEM) | Difference from 24-h control |
|---|---|---|
| Infected control - 2 h | 2.89 ± 0.07 | |
| Infected control - 24 h | 5.20 ± 0.07 | |
| caspofungin - 0.5 mg/kg | 0.33 ± 0.33 | −4.88 *** |
| caspofungin - 1.5 mg/kg | 0.73 ± 0.42 | −4.48 *** |
| caspofungin - 4.5 mg/kg | 0.00 ± 0.00 | −5.20 *** |
| compound 19 - 0.5 mg/kg | 3.01 ± 0.07 | −2.19 *** |
| compound 19 - 1.5 mg/kg | 1.74 ± 0.18 | −3.47 *** |
| compound 19 - 4.5 mg/kg | 1.17 ± 0.40 | −4.03 *** |
| compound 20 - 0.5 mg/kg | 1.96 ± 0.18 | −3.25 *** |
| compound 20 - 1.5 mg/kg | 0.73 ± 0.42 | −4.48 *** |
| compound 20 - 4.5 mg/kg | 1.45 ± 0.09 | −3.75 *** |
| compound 21 - 0.5 mg/kg | 1.57 ± 0.16 | −3.63 *** |
| compound 21 - 1.5 mg/kg | 0.73 ± 0.42 | −4.48 *** |
| compound 21 - 4.5 mg/kg | 1.17 ± 0.40 | −4.03 *** |
| compound 22 - 0.5 mg/kg | 1.65 ± 0.16 | −3.56 *** |
| compound 22 - 1.5 mg/kg | 0.00 ± 0.00 | −5.20 *** |
| compound 22 - 4.5 mg/kg | 0.65 ± 0.38 | −4.55 *** | ns, difference not significant;
*** significant at $P < 0.001$.

Fourth Run

TABLE 4

| Treatment (mg/kg) | Dose (mg/kg) | Mean log$_{10}$ CFU/kidneys (±SEM) | Difference from 24-h control |
|---|---|---|---|
| Infected control - 2 h | | 2.95 ± 0.07 | |
| Infected control - 24 h | — | 5.10 ± 0.17 | |
| anidulafungin | 0.5 | 3.81 ± 0.19 | −1.29 ** |
| anidulafungin | 1.5 | 1.08 ± 0.08 | −4.03 ** |
| compound 15 | 0.5 | 2.09 ± 0.16 | −3.01 ** |
| compound 15 | 1.5 | 1.29 ± 0.18 | −3.81 ** |
| compound 7 | 0.5 | 4.33 ± 0.17 | −0.78 * |
| compound 7 | 1.5 | 1.55 ± 0.19 | −3.55 ** |
| compound 17 | 0.5 | 3.46 ± 0.06 | −1.64 ** |
| compound 17 | 1.5 | 1.19 ± 0.12 | −3.91 ** |
| compound 8 | 0.5 | 4.78 ± 0.15 | −0.32 ns |
| compound 8 | 1.5 | 3.45 ± 0.37 | −1.66 ** |
| compound 9 | 0.5 | 5.04 ± 0.13 | −0.07 ns |
| compound 9 | 1.5 | 4.09 ± 0.23 | −1.02 ** |
| compound 10 | 0.5 | 4.89 ± 0.06 | −0.21 ns |
| compound 10 | 1.5 | 5.09 ± 0.11 | −0.01 ns |
| compound 11 | 0.5 | 4.82 ± 0.20 | −0.29 ns |
| compound 11 | 1.5 | 2.98 ± 0.03 | −2.13 ** |
| compound 18 | 0.5 | 2.54 ± 0.17 | −2.56 ** |
| compound 18 | 1.5 | 1.15 ± 0.09 | −3.95 ** |
| compound 12 | 0.5 | 3.20 ± 0.11 | −1.90 ** |
| compound 12 | 1.5 | 1.60 ± 0.09 | −3.50 ** |
| compound 13 | 0.5 | 2.81 ± 0.23 | −2.29 ** |
| compound 13 | 1.5 | 2.31 ± 0.19 | −2.80 ** |
| compound 14 | 0.5 | 4.74 ± 0.17 | −0.37 ns |
| compound 14 | 1.5 | 4.80 ± 0.34 | −0.31 ns | ns, difference not significant;
* significant at $P < 0.05$;
** significant at $P < 0.01$.

Fifth Run

TABLE 5

| Treatment (mg/kg) | Dose (mg/kg) | Mean log$_{10}$ CFU/kidneys (±SEM) | Difference from 24-h control |
|---|---|---|---|
| Infected control - 2 h | | 2.98 ± 0.06 | |
| Infected control - 24 h | — | 5.13 ± 0.15 | |
| anidulafungin | 1 | 3.06 ± 0.18 | −2.07 ** |
| compound 1 | 0.5 | 3.67 ± 0.07 | −1.47 ** |
| compound 1 | 1.5 | 1.56 ± 0.15 | −3.58 ** |
| compound 1 | 4.5 | 0.33 ± 0.33 | −4.81 ** |
| compound 16 | 0.5 | 1.91 ± 0.34 | −3.22 ** |
| compound 16 | 1.5 | 1.39 ± 0.16 | −3.74 ** |
| compound 16 | 4.5 | 1.05 ± 0.36 | −4.08 ** |

* significant at P < 0.05;
** significant at P < 0.01.

Conclusions

This mouse model was used as a primary screening tool to test the efficacy of the compounds of the invention. The mice were rendered neutropenic to ensure that the observed results are attributable to the test article and not the immune system of the mice inoculated with *C. albicans*, an organism known to accumulate in and infect the kidneys.

Kidneys were harvested from infected, but untreated control mice at 2 hours and 24 hours after infection. The kidneys were then evaluated for the fungal burden as measured in the number of colony forming units (CFU, reported in a log scale). As expected, untreated mice showed an increase in the fungal burden from 2 hours to 24 hours after the inoculation with *C. albicans*.

Infected mice receiving one of the test articles had their kidneys removed and evaluated after 24 hours, revealing varying levels of fungal burden that varied with the test article. The lower the CFU, the more efficacious the compound at treating the fungal infection in the kidneys.

The compounds that perform the best are the ones that have the best combination of the following properties: (i) activity (i.e., an inactive compound could not reduce the fungal burden), (ii) tissue penetration (i.e., a compound that does not get into the kidneys would not cure infection there), and (iii) half-life (e.g., a compound with a short half-life might not show efficacy at 24 hours).

Based upon these studies we conclude that (a) compounds 8, 9, 10, and 14 performed poorly (i.e., did not have the right combination of properties useful for treating *C. albicans* infections in this assay); (b) compounds 2, 3, 11, and 13 performed moderately, demonstrating some ability to control the *C. albicans* infection; and (c) compounds 1, 4, 5, 6, 7, 12, 15, 16, 17, 18, 19, 20, 21, and 22 performed strongly, dramatically reducing the level of *C. albicans* CFUs found in the kidneys of the mice.

Example 24

Pharmacokinetics in Beagle Dogs

The test articles were administered to beagle dogs weighing approximately 6-10 kg. Each test article was dosed at 1.4 mg/kg in aqueous saline (with or without 0.5% Tween) over course of 1-10 minutes. Diphenhydramine was kept on hand in case the dogs demonstrated a histamine response. The dogs were fasted at least 12 hours prior to each dosing and offered food after the 4-hour blood sample was taken; water was withheld for 1 hour prior to and 4 hours following each dosing event. The dose for each animal was based on its most recent body weight. The test article was injected intravenously via a catheter placed in the cephalic vein as a slow bolus.

Blood was collected via the jugular vein. All blood samples (~1 mL each) were collected into K$_3$EDTA tubes. Following blood collection, the samples were immediately inverted several times and were held on wet ice pending centrifugation. The samples were centrifuged within ~30 minutes of collection under refrigeration (~5° C. for ~10 minutes at ~2000 g) to obtain plasma. The plasma was frozen immediately on dry ice after separation. The plasma samples were stored at approximately −70° C. until analysis.

Plasma (100 µL) was precipitated with 400 µL of 0.1% formic acid in acetonitrile containing the internal standard (100 ng/mL pneumocandin). The samples were then capped and vortexed for about 30 seconds followed by centrifugation at 14,000 rpm at room temperature for 10 minutes. Following centrifugation 200 µL of supernatant was transferred to plastic autosampler vials containing 200 µL of 0.1% formic acid in water and vortexed. Samples were then analyzed by LCMSMS.

All pharmacokinetic calculations were performed using WinNonlin version 4.1 (Pharsight Corp) by noncompartmental analysis. The results are provided in Table 6, below.

TABLE 6

| | PK Values[1] | | |
|---|---|---|---|
| Compound | T ½ (hr) | Vz, (mL/Kg) | Cl (mL/hr/kg) |
| anidulafungin | 11.52 ± 0.75 | 779 ± 30.4 | 47.1 ± 1.92 |
| Compound 18 | 21.03 ± 1.16 | 687 ± 58.4 | 22.6 ± 1.08 |
| Compound 16 | 27.6 ± 1.11 | 874 ± 63.9 | 21.9 ± 0.84 |
| Compound 5 | 33.66 ± 3.28 | 627 ± 13.9 | 13.1 ± 0.94 |
| Compound 1 | 53.1 ± 3.93 | 1360 ± 61.9 | 18.06 ± 1.46 |

[1]All values are the mean ± SEM; n = 4 beagle dogs.

The observed half-life of anidulafungin was approximately 12 hours, which is consistent with previously reported values.

Compound 1 was found to have a surprisingly large volume of distribution and a surprisingly long circulating half-life. These pharmacokinetic properties may provide advantages such as decreased dosing amount, decreased dosing frequency, and/or improved efficacy in the treatment/prevention of some fungal infections.

The large volume of distribution observed for compound 1 is consistent with the distribution of this compound into certain tissues, such as kidney, liver, lung, and/or spleen. The large volume of distribution observed for compound 1 can have clinical significance for the use of this compound in treating infections localized in these tissues.

Example 25

In Vitro Activity: MEC and MIC Values Versus *Aspergillus* Spp.

MEC and MIC values (µg/mL) of anidulafungin, caspofungin, amphotericin B, compound 1, and compound 16 against various *Aspergillus* species in the presence and absence of 50% human serum were obtained as follows.

Test organisms were obtained from the American Type Culture Collection (Manassas, Va.). The isolates were maintained at −80° C., then thawed and sub-cultured prior to testing.

The MIC assay method followed the procedure described by the Clinical and Laboratory Standards Institute (see Clinical and Laboratory Standards Institute (CLSI). Reference Method for Broth Dilution Antifungal Susceptibility Testing of Yeasts; Approved Standard, Third Edition. CLSI document M27-A3 [ISBN 1-56238-666-2]. Clinical and Laboratory Standards Institute, 940 West Valley Road, Suite 1400, Wayne, Pa. 19087-1898 USA, 2008; and Clinical and Laboratory Standards Institute (CLSI). Reference Method for Broth Dilution Antifungal Susceptibility Testing of Filamentous Fungi; Approved Standard, Second Edition. CLSI document M38-A2 [ISBN 1-56238-668-9]. Clinical and Laboratory Standards Institute, 940 West Valley Road, Suite 1400, Wayne, Pa. 19087-1898 USA, 2008) and employed automated liquid handlers to conduct serial dilutions and liquid transfers. The wells in columns 1-12 in standard 96-well microdilution plates were filled with 150 µL of DMSO. These would become the 'mother plates' from which 'daughter' or test plates would be prepared. The drugs (150 µL at 80× the desired top concentration in the test plates) were dispensed into the appropriate well in column 1 of the mother plates and mixed. Serial 1:1 dilutions were made through Column 11 in the "mother plate". The wells of column 12 contained no drug and were the organism growth control wells. The daughter plates were loaded with 185 µL per well of RPMI or RPMI supplemented with 50% human serum. The daughter plates were prepared by transferring 5 µL of drug solution from each well of a mother plate to each corresponding well of each daughter plate.

Standardized inoculum of *Aspergillus* was prepared per CLSI methods. 2 mL of 0.85% saline was dispensed onto an agar slant. Using a swab, a suspension was made. After a short time to allow the heavy particles to settle out, a small quantity of the supernatant was dispensed into RPMI and the suspension adjusted to equal 0.5 McFarland turbidity. Dilutions were made for each isolate in RPMI to reach the concentration of cells described in CLSI methodology. The inoculum was dispensed into sterile reservoirs divided by length, and used to inoculate the plates. To daughter plates 10 µL of standardized inoculum was delivered into each well. Thus, the wells of the daughter plates ultimately contained 185 µL of broth, 5 µL of drug solution, and 10 µL of inoculums.

Plates were covered with a lid, placed in plastic bags, and incubated at 35° C. The *Aspergillus* plates were incubated for 48 h before reading. The microplates were viewed from the bottom using a plate viewer. For each mother plate, an un-inoculated solubility control plate was observed for evidence of drug precipitation.

Both an MIC and Minimal Effective Concentration (MEC) value was recorded. The MEC value is applied specifically to echinocandins when testing filamentous fungi. While the MIC value is the amount of drug that inhibits visible growth of the organism, the MEC value is the lowest concentration of drug that leads to the growth of small, rounded, compact hyphal forms as compared to the hyphal growth seen in the growth control well.

MEC values, which typically differ dramatically from MIC values for this class of antifungal agents, are the measure that should be used for determining susceptibility of filamentous fungi to echinocandins. The growth of the *Aspergillus* strains in each well was compared with that of the growth control at 48 hr.

The MEC and MIC values are provided in FIG. 1. This data shows that, relative to anidulafungin, compounds 1 and 16 retain their activity against *Aspergillus* strains. Thus, some modifications were made that produced profound pharmacokinetic effects without restricting activity against *Aspergillus* spp.

Example 26

In Vitro Activity: MIC Values Versus *Candida* Spp. at 24 and 48 Hours

MIC values (µg/mL) of anidulafungin, caspofungin, amphotericin B, compound 1, and compound 16 against various *Candida* species in the presence and absence of 50% human serum were obtained as follows.

Test organisms were obtained from the American Type Culture Collection (Manassas, Va.). The isolates were maintained at −80° C., then thawed and sub-cultured prior to testing.

The MIC assay method followed the procedure described by the Clinical and Laboratory Standards Institute and employed automated liquid handlers to conduct serial dilutions and liquid transfers. The wells in columns 1-12 in standard 96-well microdilution plates were filled with 150 µL of DMSO. These would become the 'mother plates' from which 'daughter' or test plates would be prepared. The drugs (150 µL at 80× the desired top concentration in the test plates) were dispensed into the appropriate well in column 1 of the mother plates and mixed. Serial 1:1 dilutions were made through Column 11 in the "mother plate". The wells of column 12 contained no drug and were the organism growth control wells. The daughter plates were loaded with 185 µL per well of RPMI or RPMI supplemented with 50% human serum. The daughter plates were prepared by transferring 5 µL of drug solution from each well of a mother plate to each corresponding well of each daughter plate.

Standardized inoculum of *Candida* was prepared per CLSI methods. For the *Candida* isolates, colonies were picked from the streak plate and a suspension was prepared in RPMI. Dilutions were made for each isolate in RPMI to reach the concentration of cells described in CLSI methodology. The inoculum was dispensed into sterile reservoirs divided by length, and used to inoculate the plates. To daughter plates 10 µL of standardized inoculum was delivered into each well. Thus, the wells of the daughter plates ultimately contained 185 µL of broth, 5 µL of drug solution, and 10 µL of inoculums.

Plates were covered with a lid, placed in plastic bags, and incubated at 35° C. The *Candida* isolates were read after 24 h incubation and again at 48 h. The microplates were viewed from the bottom using a plate viewer. For each mother plate, an un-inoculated solubility control plate was observed for evidence of drug precipitation.

For *Candida* species, the Minimal Inhibitory Concentration (MIC) was read per CLSI guidelines. The MIC was defined as the lowest concentration of an antifungal agent that substantially inhibits growth of the organism as detected visually (MIC values are provided in FIG. 2).

This data shows that, relative to anidulafungin, compounds 1 and 16 retain their activity against *Candida* strains. Thus, some modifications were made that produced profound pharmacokinetic effects without restricting activity against *Candida* spp.

Serum is known to differentially alter the antifungal properties of echinocandin drugs (see Paderu et al., Antimicrob Agents Chemother. 51:2253 (2007)). Compounds 1 and 16 were found to have superior activity against a strain of *Candida glabrata* in 50% human serum in comparison to the performance of anidulafungin under these same conditions. This difference in activity can be clinically relevant to the use of these compounds for the treatment of certain blood stream infections.

Example 27

Amphiphilicity of Compound 1

The solubility of compound 1 (acetate salt) was measured in aqueous buffers of varying pH to assess this compound's suitability for formulation in an aqueous carrier for administration by injection (e.g., intravenous or intramuscular injection).

The results are provided in Table 7 (below) along with anidulafungin as a comparison. Compound 1 was found to have dramatically greater aqueous solubility than anidulafungin over a broad pH range.

TABLE 7

| | Solubility (mg/mL)[1] | |
|---|---|---|
| pH | Anidulafungin | Compound 1 |
| 1 (0.1M HCl) | <0.01 | >15 |
| 3 (0.01M formate buffer) | <0.01 | >15 |
| 4.6 (0.1M acetate buffer) | <0.01 | >15 |
| 5.6 (0.1M acetate buffer) | <0.01 | >15 |
| 7.4 (0.1M phosphate buffer) | <0.01 | 0.05 |
| 8.5 (0.01M TRIS buffer) | <0.01 | >15 |
| 0.9% saline | <0.01 | 4.6 |

[1]All measurements made at ambient temperature

The solubility of compound 1 (acetate salt) was also measured in non-aqueous solvents to assess this compound's suitability for formulation in non-aqueous carriers. The results are provided in Table 8 (below).

TABLE 8

| | Solubility (mg/mL) | |
|---|---|---|
| pH | Anidulafungin | Compound 1 |
| Propylene glycol(PG) | >17.2 | >18.4 |
| Ethanol (EtOH) | >17.6 | >13.7 |
| Glycerol | 1.5 | >19.4 |
| PEG400 | >26.8 | >34.1 |

Example 28

Synthesis of Compound 23

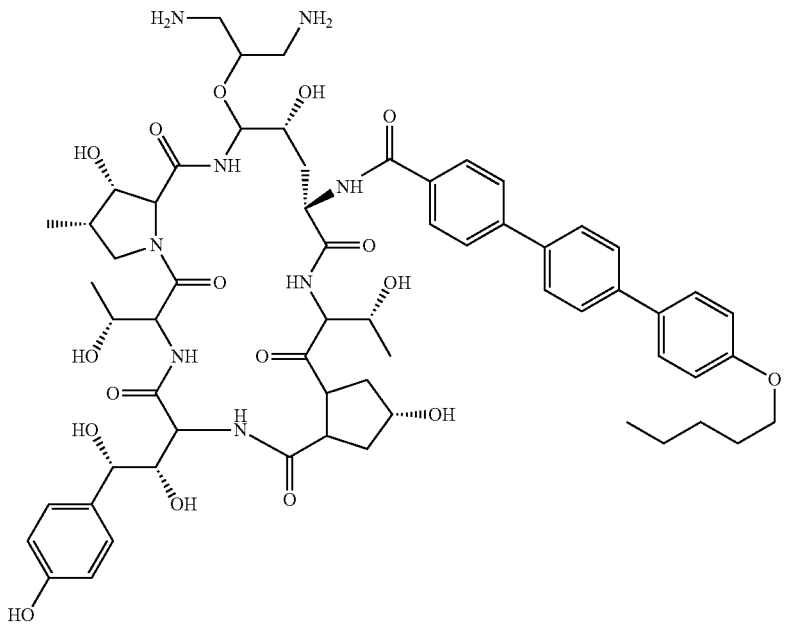

(23)

Anidulafungin (20 mg; 0.018 mmol) in $CH_3CN$ (10 ml) was treated with phenylboronic acid (2.5 mg; 0.021 mmol) and the mixture was stirred for 30 minutes. The resulting solution was concentrated in vacuo to dryness, and the solids were taken up in a solution of DMSO (0.3 mL) and 1,3-diamino-2-propanol hydrochloride. The mixture was titrated with HCl (4M in dioxane) until acidic on wet pH paper. The resulting solution was heated at 40-45° C. for 8 days then diluted with water and purified by preparative RP HPLC eluting with water (0.1% TFA)/$CH_3CN$ (0.1% TFA). The product was isolated by freeze-drying to give 33 mg of compound 23 as a white solid. HPLC $T_R$ 11.28 min (93%). LC/MS, ESI+/− m/z 1212.58 $[M+H]^+$, 1210.57 $[M−H]^−$.

Example 29

Synthesis of Compound 24

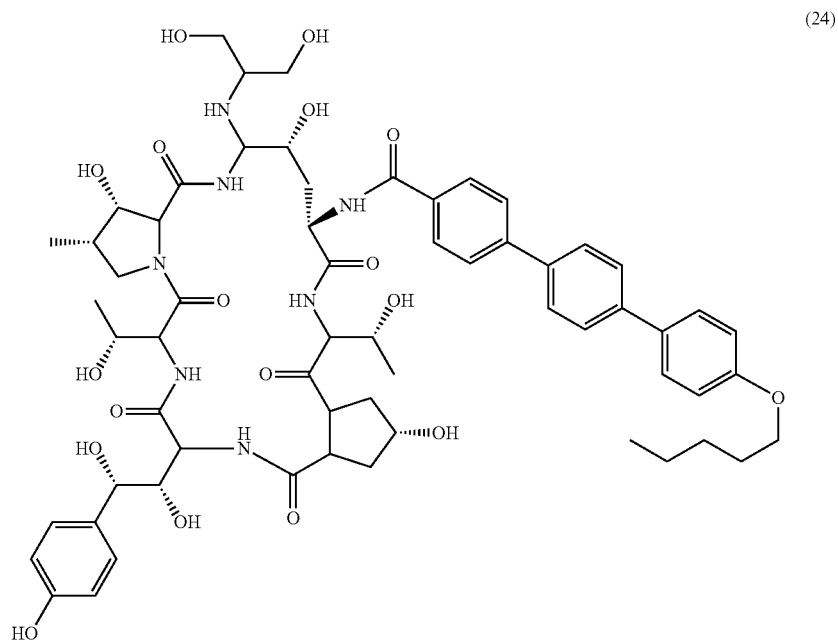 [SMILES: CCCCCOc1ccc(-c2ccc(-c3ccc(C(=O)N[C@H]4C[C@@H](O)C(NC(CO)CO)NC(=O)C5[C@@H](O)[C@@H](C)CN5C(=O)C([C@@H](C)O)NC(=O)C([C@H](O)[C@@H](O)c5ccc(O)cc5)NC(=O)C5C[C@@H](O)CC5C(=O)C([C@@H](C)O)NC4=O)cc3)cc2)cc1]

(24)

Anidulafungin hemiaminal-(4-methoxy)phenylthioether (20 mg; 0.016 mmol) was mixed with serinol (114 mg) and dry DMSO (15 μL). The mixture was capped under argon and heated to 70° C. for 2.5 hours. The reaction was diluted with methanol and water, acidified by addition of TFA, further diluted with water, and purified by preparative RP HPLC eluting with $CH_3CN/H_2O$ and 0.1% TFA. Purified product was isolated by freeze-drying to give 13 mg of compound 24 as a white solid. HPLC $T_R$ 10.71 min (94% @ 220 nm). LC/MS, ESI+/− m/z 1213.57 [M+H]$^+$, 1211.56 [M−H]$^−$.

Example 30

Separation of Isomers

Figure 3B:
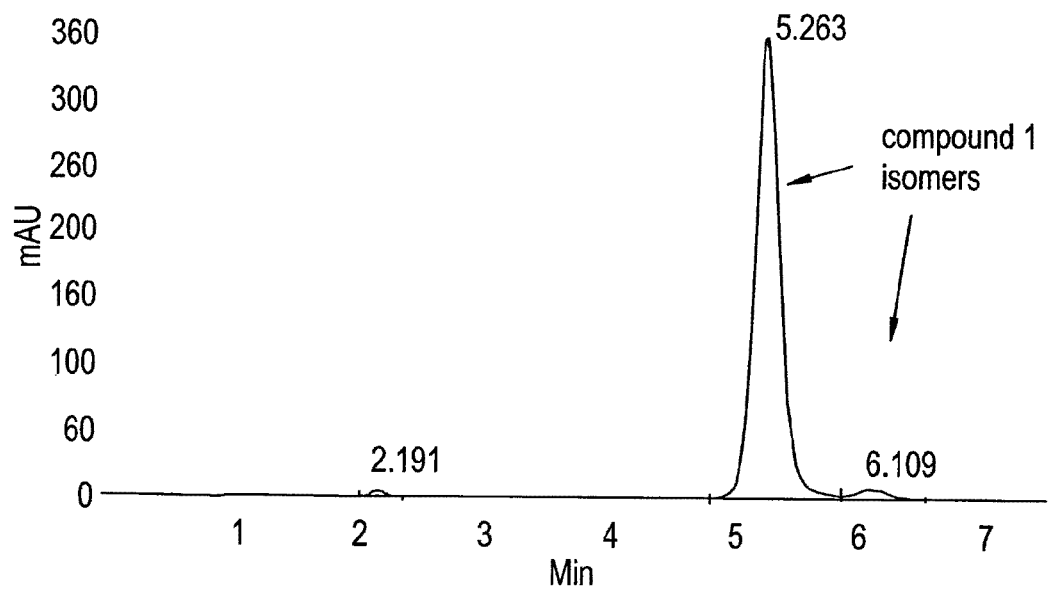

Compound 1 purified by preparative RP HPLC eluting with $CH_3CN/H_2O$ and 0.1% TFA was found to be a mixture of isomers (see FIGS. 3A and 3B). The two isomers observed are believed to differ in stereochemistry where the choline substituent is attached to the anidulafungin starting material (see the isomers depicted below).

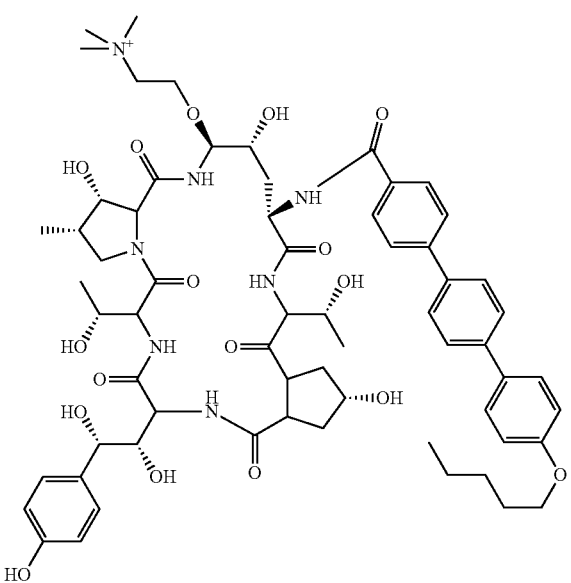

(1a)

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A compound described by formula (Ia):

wherein,
$R^1$ is $O(CH_2CH_2O)_nCH_2CH_2X_1$, $O(CH_2CH_2CH_2O)_n$ $CH_2CH_2X_1$, $NHCH_2CH_2X_2$, $NH(CH_2CH_2O)_m$ $CH_2CH_2X_2$, $NH(CH_2CH_2CH_2O)_mCH_2CH_2X_2$, $NH(CH_2CH_2O)_pCH_2CH_2X_3$, $NH(CH_2CH_2CH_2O)_p$ $CH_2CH_2X_3$, $NH[CH_2(CH_2)_aO]_bCH\{CH_2[OCH_2(CH_2)_c]_dX_5\}_2$, $O[CH_2(CH_2)_aO]_bCH\{CH_2[OCH_2(CH_2)_c]_dX_5\}_2$, $NH(CH_2CH_2NH)_rCH_2CH_2X_5$, $NHCH_2(CH_2)_qX_6$, or $OCH_2(CH_2)_qX_6$;
$R^T$ is n-pentyl, sec-pentyl, or iso-pentyl;
$X_1$ is $NH_2$, $NHR^{A1}$, $NR^{A1}R^{A2}$, or $NR^{A1}R^{A2}R^{A3}$;
$X_2$ is OH or $OR^{B1}$;
$X_3$ is $NH_2$, $NHR^{C1}$, $NR^{C1}R^{C2}$, or $NR^{C1}R^{C2}R^{C3}$;
each $X_5$ is, independently, selected from OH, $OR^{E1}$, $NH_2$, $NHR^{E1}$, $NR^{E1}R^{E2}$, or $NR^{E1}R^{E2}R^{E3}$;
$X_6$ is selected from $NR^{F1}R^{F2}R^{F3}$;
a is an integer from 1 to 2;
b is an integer from 0 to 3;
c is an integer from 1 to 2;
d is an integer from 0 to 3;
n is an integer from 1 to 5;
m is an integer from 1 to 5;
p is an integer from 1 to 5;
r is an integer from 1 to 5;
q is an integer from 1 to 3; and
each of $R^{A1}$, $R^{A2}$, $R^{A3}$, $R^{B1}$, $R^{C1}$, $R^{C2}$, $R^{C3}$, $R^{E1}$, $R^{E2}$, $R^{E3}$, $R^{F1}$, $R^{F2}$, and $R^{F3}$ is, independently, selected from $CH_3$, $CH_2CH_3$, $CH_2CH_2CH_3$, or $CH(CH_3)_2$, or a pharmaceutically acceptable salt thereof, wherein the compound is not compound 1 or a pharmaceutically acceptable salt thereof.

2. The compound of claim 1, wherein one of $X_1$, $X_3$, $X_5$, and $X_6$ is selected from $N(CH_3)_3^+$ or $N(CH_2CH_3)_3^+$.

3. The compound of claim 1, wherein $R^1$ is selected from $NHCH_2(CH_2)_qX_6$, $O(CH_2CH_2O)_nCH_2CH_2X_1$, or $OCH_2(CH_2)_qX_6$.

4. The compound of claim 3, wherein $R^1$ is $NHCH_2(CH_2)_qX_6$; q is an integer from 1 to 3; and $X_6$ is $N(CH_3)_3^+$ or $N(CH_2CH_3)_3^+$.

5. The compound of claim 4, wherein q is 1; and $X_6$ is $N(CH_3)_3^+$ or a pharmaceutically acceptable salt thereof.

6. The compound of claim 3, wherein $R^1$ is $O(CH_2CH_2O)_nCH_2CH_2X_1$; n is an integer from 1 to 5; and $X_1$ is $NH_2$.

7. The compound of claim 6, wherein n is 1 or a pharmaceutically acceptable salt thereof.

8. The compound of claim 3, wherein $R^1$ is $OCH_2(CH_2)_qX_6$; q is an integer from 1 to 3; and $X_6$ is $N(CH_3)_3^+$ or $N(CH_2CH_3)_3^+$.

9. Compound 5 or a pharmaceutically acceptable salt thereof.

10. Compound 16 or a pharmaceutically acceptable salt thereof.

11. Compound 18 or a pharmaceutically acceptable salt thereof.

12. A compound selected from compound 6, compound 7, compound 12, compound 15, compound 17, compound 23, compound 24, or pharmaceutically acceptable salts thereof.

13. A pharmaceutical composition comprising a compound of claim 1, or a pharmaceutically acceptable salt thereof, and a pharmaceutically acceptable excipient.

14. The pharmaceutical composition of claim 13, wherein said compound is an acetate salt or chloride salt.

15. A method of treating a fungal infection in a subject, said method comprising administering to said subject a pharmaceutical composition of claim 13 in an amount sufficient to treat said infection.

16. The method of claim 15, wherein said pharmaceutical composition is administered intravenously.

17. The method of claim 15, wherein said pharmaceutical composition is administered topically.

18. The method of claim 15, wherein said pharmaceutical composition is administered subcutaneously.

19. The method of claim 15, wherein said pharmaceutical composition is administered orally.

20. method of claim 15, wherein said pharmaceutical composition is administered intramuscularly.

21. The method of claim 15, wherein said pharmaceutical composition is administered by way of inhalation.

22. The method of claim 15, wherein said pharmaceutical composition is administered to treat a blood stream infection or tissue infection in said subject.

23. The method of claim 15, wherein said infection is selected from tinea capitis, tinea corporis, tinea pedis, onychomycosis, perionychomycosis, pityriasis versicolor, oral thrush, vaginal candidosis, respiratory tract candidosis, biliary candidosis, eosophageal candidosis, urinary tract candidosis, systemic candidosis, mucocutaneous candidosis, aspergillosis, mucormycosis, paracoccidioidomycosis, North American blastomycosis, histoplasmosis, coccidioidomycosis, sporotrichosis, fungal sinusitis, or chronic sinusitis.

24. The method of claim 15, wherein wherein said fungal infection is an infection of *Candida albicans, C. parapsilosis, C. glabrata, C. guilliermondii, C. krusei, C. tropicalis, C. lusitaniae, Aspergillus fumigatus, A. flavus, A. terreus, A. niger, A. candidus, A. clavatus*, or *A. ochraceus*.

25. A method of preventing a fungal infection in a subject, said method comprising administering to said subject a pharmaceutical composition of claim 13 in an amount sufficient to prevent said infection.

26. The method of claim 25, wherein said pharmaceutical composition is administered intravenously.

27. The method of claim 25, wherein said pharmaceutical composition is administered topically.

28. The method of claim 25, wherein said pharmaceutical composition is administered subcutaneously.

29. The method of claim 25, wherein said pharmaceutical composition is administered orally.

30. The method of claim 25, wherein said pharmaceutical composition is administered intramuscularly.

31. The method of claim 25, wherein said pharmaceutical composition is administered by way of inhalation.

32. The method of claim 25, wherein said subject is being prepared for an invasive medical procedure, said subject is immunocompromised, or said subject is undergoing long term antibiotic therapy.

33. The method of claim 15, wherein said pharmaceutical composition comprises a compound selected from compound 5, compound 16, or pharmaceutically acceptable salts thereof.

34. A method of preventing, stabilizing, or inhibiting the growth of fungi, or killing fungi, said method comprising contacting said fungi or a site susceptible to fungal growth with a compound of any of claim 1 or a pharmaceutically acceptable salt thereof.

* * * * *